United States Patent
McRae et al.

(10) Patent No.: US 10,953,011 B2
(45) Date of Patent: Mar. 23, 2021

(54) METHODS OF TREATING VIRALLY ASSOCIATED CANCERS WITH HISTONE DEACETYLASE INHIBITORS

(71) Applicant: Viracta Therapeutics Inc., Cardiff, CA (US)

(72) Inventors: Robert McRae, Cardiff, CA (US); Gail L. Brown, Cardiff, CA (US); Xiaohu Deng, Cardiff, CA (US); David Slack, Cardiff, CA (US); Marshelle Smith Warren, Cardiff, CA (US); Richard Trauger, Cardiff, CA (US)

(73) Assignee: VIRACTA THERAPEUTICS INC., Cardiff (CA)

( * ) Notice: Subject to any disclaimer, the term of this patent is extended or adjusted under 35 U.S.C. 154(b) by 0 days.

(21) Appl. No.: 16/924,082

(22) Filed: Jul. 8, 2020

(65) Prior Publication Data

US 2020/0375990 A1  Dec. 3, 2020

Related U.S. Application Data

(63) Continuation of application No. PCT/US2020/034951, filed on May 28, 2020.

(60) Provisional application No. 62/855,454, filed on May 31, 2019.

(51) Int. Cl.
| | |
|---|---|
| *A61K 31/506* | (2006.01) |
| *A61K 31/4709* | (2006.01) |
| *A61P 35/00* | (2006.01) |
| *A61K 31/522* | (2006.01) |
| *A61K 9/00* | (2006.01) |

(52) U.S. Cl.
CPC .......... *A61K 31/506* (2013.01); *A61K 31/522* (2013.01); *A61P 35/00* (2018.01); *A61K 9/0053* (2013.01); *A61K 31/4709* (2013.01)

(58) Field of Classification Search
CPC .... A61K 31/506; A61K 31/4709; A61P 35/00
See application file for complete search history.

(56) References Cited

U.S. PATENT DOCUMENTS

| | | |
|---|---|---|
| 3,471,513 A | 10/1969 | Leland |
| 3,904,612 A | 9/1975 | Nagasawa et al. |
| 4,008,323 A | 2/1977 | Cousse et al. |
| 4,011,336 A | 3/1977 | Amann et al. |
| 4,026,895 A | 5/1977 | Tanaka et al. |
| 4,031,243 A | 6/1977 | Aparicio et al. |
| 4,058,558 A | 11/1977 | Cousse et al. |
| 4,131,617 A | 12/1978 | Esanu |
| 4,176,193 A | 11/1979 | Esanu |
| 4,234,599 A | 11/1980 | Van Scott et al. |
| 4,613,616 A | 9/1986 | Winston et al. |
| 4,671,901 A | 6/1987 | Green |
| 4,699,926 A | 10/1987 | Abraham et al. |
| 4,704,402 A | 11/1987 | Abraham et al. |
| 4,723,958 A | 2/1988 | Pope et al. |
| 4,731,381 A | 3/1988 | Abraham et al. |
| 4,732,914 A | 3/1988 | Morton, Jr. |
| 4,735,967 A | 4/1988 | Neesby |
| 4,747,825 A | 5/1988 | Linkie et al. |
| 4,751,244 A | 6/1988 | Abraham et al. |
| 4,766,116 A | 8/1988 | Tatsuoka et al. |
| 4,820,711 A | 4/1989 | Pearlman |
| 4,822,821 A | 4/1989 | Perrine |
| 4,849,426 A | 7/1989 | Pearlman |
| 4,851,229 A | 7/1989 | Magruder et al. |
| 4,853,388 A | 8/1989 | Pearlman |
| 4,880,624 A | 11/1989 | Metcalf et al. |
| 4,894,364 A | 1/1990 | Greer |
| 4,925,873 A | 5/1990 | Friedhoff et al. |
| 4,948,592 A | 8/1990 | Ayer et al. |
| 4,952,560 A | 8/1990 | Kigasawa et al. |
| 4,958,592 A | 9/1990 | Anthony et al. |
| 4,965,251 A | 10/1990 | Stamatoyannopoulos |
| 4,997,815 A | 3/1991 | Perrine et al. |
| 5,023,251 A | 6/1991 | Sattler et al. |
| 5,025,029 A | 6/1991 | Perrine |
| 5,032,307 A | 7/1991 | Carlson |
| 5,039,703 A | 8/1991 | Breuer |
| 5,081,124 A | 1/1992 | Hughes |
| 5,100,647 A | 3/1992 | Agus et al. |
| 5,137,734 A | 8/1992 | Spiegelman et al. |
| 5,185,436 A | 2/1993 | Villa et al. |
| 5,190,029 A | 3/1993 | Byron et al. |
| 5,199,942 A | 4/1993 | Gillis |
| 5,208,333 A | 5/1993 | Paul et al. |
| 5,216,004 A | 6/1993 | Perrine |

(Continued)

FOREIGN PATENT DOCUMENTS

| | | |
|---|---|---|
| CA | 1209037 A1 | 8/1986 |
| CA | 2173976 A1 | 4/1995 |

(Continued)

OTHER PUBLICATIONS

Chan et al., Chidamide in the treatment of peripheral T-cell lymphoma. Onco Targets Ther. 10:347-352 (2017).
Hui et al., Inhibition of class I histone deacetylases by romidepsin potently induces Epstein-Barr virus lytic cycle and mediates enhanced cell death with ganciclovir. Int J Cancer. 138(1):125-136 (2016).
PCT/US2020/034951 International Search Report and Written Opinion dated Aug. 7, 2020.

(Continued)

*Primary Examiner* — Samira J Jean-Louis
(74) *Attorney, Agent, or Firm* — Wilson Sonsini Goodrich & Rosati

(57) ABSTRACT

Described herein are certain dosing schedules and amounts that effectively prevent and manage side effects associated with histone deacetylase inhibitor (HDACi) treatment. Optionally, these schedules and dosing regimens include treatment with an antiviral agent.

25 Claims, 4 Drawing Sheets

(56) References Cited

U.S. PATENT DOCUMENTS

| | | |
|---|---|---|
| 5,258,367 A | 11/1993 | Bazer et al. |
| 5,270,458 A | 12/1993 | Lemischka |
| 5,366,996 A | 11/1994 | Elford et al. |
| 5,376,359 A | 12/1994 | Johnson |
| 5,378,716 A | 1/1995 | Hamanaka et al. |
| 5,403,590 A | 4/1995 | Forse |
| 5,403,867 A | 4/1995 | Okumura et al. |
| 5,468,731 A | 11/1995 | Matsuo et al. |
| 5,635,532 A | 6/1997 | Samid |
| 5,654,333 A | 8/1997 | Samid |
| 5,661,179 A | 8/1997 | Samid |
| 5,674,898 A | 10/1997 | Cheng et al. |
| 5,674,912 A | 10/1997 | Martin |
| 5,679,707 A | 10/1997 | Okumura et al. |
| 5,710,175 A | 1/1998 | Nudelman et al. |
| 5,710,178 A | 1/1998 | Samid |
| 5,750,571 A | 5/1998 | Cheng et al. |
| 5,776,434 A | 7/1998 | Purewal et al. |
| 5,780,451 A | 7/1998 | Demichele et al. |
| 5,843,994 A | 12/1998 | Samid |
| 5,846,528 A | 12/1998 | Podsakoff et al. |
| 5,852,056 A | 12/1998 | Samid |
| 5,858,365 A | 1/1999 | Faller |
| 5,883,123 A | 3/1999 | Tung et al. |
| 5,912,269 A | 6/1999 | Tung et al. |
| 5,932,545 A | 8/1999 | Henkin et al. |
| 5,939,456 A | 8/1999 | Perrine |
| 5,945,407 A | 8/1999 | Bemis et al. |
| 5,952,314 A | 9/1999 | Demichele et al. |
| 6,011,000 A | 1/2000 | Perrine et al. |
| 6,030,961 A | 2/2000 | Nudelman et al. |
| 6,043,389 A | 3/2000 | Nudelman et al. |
| 6,197,743 B1 | 3/2001 | Faller |
| 6,231,880 B1 | 5/2001 | Perrine |
| 6,403,647 B1 | 6/2002 | Perrine |
| 6,451,334 B2 | 9/2002 | Perrine |
| 6,677,302 B2 | 1/2004 | Faller |
| 7,192,715 B2 | 3/2007 | Harley et al. |
| 7,265,153 B2 | 9/2007 | Faller et al. |
| 7,932,246 B2 | 4/2011 | Moffat et al. |
| 8,242,172 B2 | 8/2012 | Perrine |
| 8,618,068 B2 | 12/2013 | Perrine et al. |
| 8,993,581 B2 | 3/2015 | Perrine et al. |
| 2001/0009922 A1 | 7/2001 | Faller |
| 2001/0027215 A1 | 10/2001 | Perrine |
| 2003/0018069 A1 | 1/2003 | Faller et al. |
| 2003/0077297 A1 | 4/2003 | Chen et al. |
| 2005/0025839 A1 | 2/2005 | Polli |
| 2005/0272644 A1 | 12/2005 | Chung |
| 2006/0074046 A1 | 4/2006 | Redkar et al. |
| 2007/0072793 A1 | 3/2007 | Chung |
| 2007/0232528 A1 | 10/2007 | Franke |
| 2008/0015190 A1 | 1/2008 | Chakravarty et al. |
| 2008/0027136 A1 | 1/2008 | Faller et al. |
| 2008/0057086 A1 | 3/2008 | Etter |
| 2008/0146591 A1 | 6/2008 | Bachynsky et al. |
| 2008/0175849 A1 | 7/2008 | Smith et al. |
| 2008/0207590 A1 | 8/2008 | Deziel et al. |
| 2008/0254026 A1 | 10/2008 | Long et al. |
| 2009/0048300 A1 | 2/2009 | Chen et al. |
| 2009/0082444 A1 | 3/2009 | Perrine et al. |
| 2009/0130134 A1 | 5/2009 | Pancre et al. |
| 2009/0131367 A1 | 5/2009 | Gore et al. |
| 2009/0270497 A1 | 10/2009 | Buggy |
| 2009/0298924 A1 | 12/2009 | Davidson et al. |
| 2010/0010010 A1 | 1/2010 | Davidson et al. |
| 2010/0152155 A1 | 6/2010 | Moffat et al. |
| 2010/0168004 A1 | 7/2010 | Williams et al. |
| 2010/0280113 A1 | 11/2010 | Faller et al. |
| 2010/0317678 A1 | 12/2010 | Moffat et al. |
| 2011/0033946 A1 | 2/2011 | Berenson et al. |
| 2011/0086869 A1 | 4/2011 | Perrine et al. |
| 2011/0245154 A1 | 10/2011 | Berenson et al. |
| 2011/0251149 A1 | 10/2011 | Perrine et al. |
| 2012/0310183 A1 | 12/2012 | Epner et al. |
| 2013/0331313 A1 | 12/2013 | Berenson et al. |
| 2014/0045774 A1 | 2/2014 | Perrine et al. |
| 2014/0170221 A1 | 6/2014 | Irvine et al. |
| 2014/0341989 A1 | 11/2014 | Loury et al. |
| 2016/0113929 A1 | 4/2016 | Berenson et al. |
| 2016/0317624 A1 | 11/2016 | Casebolt et al. |
| 2017/0042898 A1 | 2/2017 | Berenson et al. |
| 2017/0210786 A1 | 7/2017 | Nussenzweig et al. |
| 2018/0185345 A1 | 7/2018 | Faller |

FOREIGN PATENT DOCUMENTS

| | | |
|---|---|---|
| CA | 2303268 A1 | 12/1998 |
| CA | 3002755 A1 | 5/2017 |
| CN | 102391359 A | 3/2012 |
| CN | 102793693 A | 11/2012 |
| CN | 103232474 A | 8/2013 |
| CN | 105055386 A | 11/2015 |
| CN | 105617381 A | 6/2016 |
| CN | 108347929 A | 7/2018 |
| EP | 0069659 A1 | 1/1983 |
| EP | 0224599 A1 | 6/1987 |
| EP | 0320726 A2 | 6/1989 |
| EP | 0324574 A2 | 7/1989 |
| EP | 0320726 A3 | 8/1990 |
| EP | 0350287 A3 | 8/1990 |
| EP | 0324574 A3 | 12/1990 |
| EP | 0546261 A2 | 6/1993 |
| EP | 0546261 A3 | 8/1993 |
| EP | 0617966 A1 | 10/1994 |
| EP | 0371789 B1 | 1/1997 |
| EP | 2683371 A1 | 1/2014 |
| GB | 2126082 A | 3/1984 |
| JP | S5089335 A | 7/1975 |
| JP | S61180740 A | 8/1989 |
| JP | 6208667 B2 | 10/2017 |
| KR | 20150029678 A | 3/2015 |
| RU | 2555474 C1 | 7/2015 |
| WO | WO-9011071 A1 | 10/1990 |
| WO | WO-9101719 A1 | 2/1991 |
| WO | WO-9203155 A1 | 3/1992 |
| WO | WO-9204913 A1 | 4/1992 |
| WO | WO-9307866 A2 | 4/1993 |
| WO | WO-9318761 A1 | 9/1993 |
| WO | WO-9404671 A1 | 3/1994 |
| WO | WO-9510271 A2 | 4/1995 |
| WO | WO-9511699 A1 | 5/1995 |
| WO | WO-9510271 A3 | 6/1995 |
| WO | WO-9602244 A1 | 2/1996 |
| WO | WO-9627369 A2 | 9/1996 |
| WO | WO-9627369 A3 | 11/1996 |
| WO | WO-9704761 A1 | 2/1997 |
| WO | WO-9804290 A2 | 2/1998 |
| WO | WO-9804290 A3 | 8/1998 |
| WO | WO-9840078 A1 | 9/1998 |
| WO | WO-9856370 A2 | 12/1998 |
| WO | WO-9856370 A3 | 4/1999 |
| WO | WO-2007133653 A3 | 1/2008 |
| WO | WO-2008097654 A1 | 8/2008 |
| WO | WO-2011072086 A1 | 6/2011 |
| WO | WO-2011113013 A2 | 9/2011 |
| WO | WO-2013110280 A1 | 8/2013 |
| WO | WO-2013181584 A2 | 12/2013 |
| WO | WO-2014085546 A1 | 6/2014 |
| WO | WO-2016205695 A1 | 12/2016 |
| WO | WO-2017197303 A1 | 11/2017 |
| WO | WO-2018013962 A1 | 1/2018 |

OTHER PUBLICATIONS

Porcu et al., A Phase 1B/2 Study of Oral Nanatinostat (N) and Valganciclovir (VG) in Subjects With Epstein-Barr Virus (EBV)-Associated Lymphomas. Journal of Clinical Oncology 37(15): Abstract (2019).

Porcu et al., Combination of Oral Nanatinostat (Nstat), a Novel Histone Deacetylase Inhibitor (HDACi), and the Oral Anti-Viral, Valganciclovir (VGCV), Is Active in Relapsed/Refractory (R/R) Epstein-Barr Virus (EBV)-Positive B-Cell, T-Cell, and Hodgkin

(56) References Cited

OTHER PUBLICATIONS

Lymphoma: Interim Safety and Efficacy Results from a Phase 1b/2a Study. Blood 134(Supplement1):465 (2019).

Abbott, et al. Quantitative structure-anticonvulsant activity relationships of valproic acid, related carboxylic acids and tetrazoles. Neuropharmacology. Mar. 1988;27(3):287-94.

Abe, et al. Sodium butyrate induction of milk-related antigens in human MCF-7 breast carcinoma cells. Cancer Research. Oct. 1984;44:4574-4577.

Abraham, et al. Design, synthesis, and testing of potenital antisickling agents. 1. Halogenated Benzyloxy and Phenoxy Acids. J. Med. Chem. 1982;25:1015-17.

Anderson, et al. Molecular cloning of mast cell growth factor, a hematopoietin that is active in both membrane bound and soluble forms. Cell. Oct. 5, 1990;63:235-243.

Andrews, et al. A rapid micropreparation technique for extraction of DNA-binding proteins from limiting numbers of mammalian cells. Nucl. Acids Res. 1991;19:2499-2500.

Andrews, et al. Erythroid transcription factor NF-E2 is a haematopoietic-specific basic-leucine zipper protein. Nature. 1993;362:722-728.

Antoni, et al. NF-.kappa. B-Dependent and -Independent Pathways of HIV Activation in a Chronically Infected T Cell Line. Virology. 1994;202:684-694.

Archin, et al. Antiretroviral intensification and valproic acid lack sustained effect on residual HIV-1 viremia or resting CD4+ cell infection. PLoS One. Feb. 23, 2010;5(2):e9390 (p. 1-4).

Archin, et al. Expression of latent HIV induced by the potent HDAC inhibitor suberoylanilide hydroxamic acid. AIDS Res Hum Retroviruses. Feb. 2009;25(2):207-12.

Archin, et al. Expression of latent human immunodeficiency type 1 is induced by novel and selective histone deacetylase inhibitors. AIDS. Sep. 10, 2009;23(14):1799-806.

Archin, et al. Valproic acid without intensified antiviral therapy has limited impact on persistent HIV infection of resting CD4+ T cells. AIDS. Jun. 19, 2008;22(10):1131-5.

Armstrong, et al. Criteria for the definition of Epstein-Barr virus association in Hodgkin's disease. Leukemia. 6(9):869-874.

Augeron, et al. Emergence of permanently differentiated cell clones in a human colonic cancer cell line in culture after treatment with sodium butyrate. Cancer Research. Sep. 1984;44:3961-3969.

Bangham et al. Diffusion of univalent ions across the lamellae of swollen phospholipids. J. Mol. Biol. 1965;13:238-252.

Barbul, et al. Arginine enhances wound healing and lymphocyte immune responses in humans. Surgery. Aug. 1990;108(2):331-6; discussion 336-7.

Barker, et al. The actions of cyclic AMP, its butyryl derivatives and Na butyrate on the proliferation of malignant trophoblast cells in vitro, Br. J. Cancer. 1977;35:314-321.

Barton, et al. The erythroid protein cGATA-1 Functions with a stage-specific factor to activate transcription of chromatin-assembled b-globin genes. Genes & Development. 1993;7:1796-809.

Bartram, et al. Proliferation of human colonic mucosa as an intermediate biomarker of carcinogenesis: effects of butyrate, deoxycholate, calcium, ammonia, and pH. Cancer Research. Jul. 15, 1993;53:3283-3288.

Basson, et al. Butyrate-induced enterocyte differentiation and mucosal wound healing. Gastroenterology. 1993; 104(4) supp.:A235.

Belcheva, et al. Up-regulation of delta opioid receptors in neuroblastoma hybrid cells: evidence for differences in the mechanisms of action of sodium butyrate and naltrexone. J Pharmacol Exp Ther. Oct. 1991;259(1):302-9.

Bernards, et al. Physical mapping of the globin gene deletion in hereditary persistence of foetal haemoglobin (HPFH). Nucleic Acids Research. 1980;8(7):1521-1534.

Bingham. Patty's Toxicology. John Wiley and Sons, Incorporated. Jan. 1, 2001;5:707-711.

Bloch. Induced cell differentiation in cancer therapy. Cancer Treatment Reports. 1984;68:199-205.

Bohan, et al. Mutational analysis of sodium butyrate inducible elements in the human immunodeficiency virus type 1 long terminal repeat. Virology. 1989;172:573-583.

Bohan, et al. Sodium butyrate activates human immunodeficiency virus long terminal repeat-directed expression. Biochem and Biophys. Res. Comm. 1987;148(3):899-905.

Bonnet et al., Detection of Epstein-Barr virus in invasive breast cancers. J Nat Cancer Inst. 91(16):1376-1381 (1999).

Boosalis, et al. Short-chain fatty acid derivatives stimulate cell proliferation and induce Stat-5 activation. Blood. May 15, 2001;97(10):3259-67.

Boulikas. Poly (ADP-ribose) synthesis in blocked and damaged cells and its relation to carcinogenesis. Anticancer Res. 1992;12(3):885-898.

Bourgeade, et al. Effect of sodium butyrate on the antiviral and anticellular action of interferon in normal and MSV-transformed cells. Int J Cancer. Sep. 15, 1979;24(3):314-8.

Bourgeade, et al. Enhancement of interferon anti-tumor action by sodium butyrate. Cancer Res. 1979;39:4720-4723.

Breitman, et al. Combinations of retinoic acid with either sodium butyrate, dimethyl, sulfoxide, or hexamethylene bisacetamide synergistically induce differentiation of the human myeoid leukemia cell line HL60. Cancer Research. 1990;50:6268-6273.

Breuer, et al. Rectal irrigation with short-chain fatty acids for distal ulcerative colitis. Dig. Dis. Sci.1991;36(2):185-187.

Briz et al., Epstein-Barr virus associated B-cell lymphoma after autologous bone marrow transplantation for T-cell acute lymphoblastic leukaemia. British Journal of Haematology. 98(2):485-487 (1997).

Brooks, et al. Epstein-Barr virus and lymphomas. Cancer Surv. 1999;33:99-123.

Brousset, et al. Detection of Epstein-Barr virus messenger RNA in Reed-Sternberg cells of Hodgkin's disease by in situ hybridization with biotinylated probes on specially processed modified acetone methyl benzoate xylene (ModAMeX) sections. Blood. 1991;77:1781-1786.

Bugaut, et al. Biological effects of short-chain fatty acids in non-ruminant mammals. Amex. Rev. Nutr.1993;13:217-241.

Burkitt, A sarcoma involving the jaws in African children. The British Journal of Surgery. 46(127):218-223 (1958).

Burns, et al. Butyrate induces selective transcriptional activation of a hypomethylated embryonic globin gene in adult erythroid cells. Blood. 1988;72(5):1536-1542.

Byrd, et al. Two types of transglutaminase in the PC12 pheochromocytoma cell line. The Journal of Biological Chemistry. Aug. 25, 1987;262(24):11699-11705.

Callery, et al. Identification of metabolites of the cell-differentiating agent hexamethylene bisacetamide in humans. Cancer Res. 1986;46:4900-4903.

Canceill, et al. Stereochimstry of the reduction of b-keto esters, p-keto amides, and b-keto nitriles by hydrides. Bull. Soc. Chim. 1970 Fr. 6:2180-2187. (Abstract only).

Caruso, et al. Regression of established macroscopic liver metastases after in situ transduction of a suicide gene. Proc Natl Acad Sci USA. Aug. 1, 1993;90(15):7024-8.

Chany, et al. Antitumor effect of arginine butyrate in conjunction with corynebacterium and interferon. Int. J. Cancer. 1982;30:489-93.

Chany, et al. Effect of coordinated therapeutic assays using C. Parvum, Interferon and Arginine Butyrate on spontaneous disease and survival of AKR mice. Int. J. Cancer. 1993;32:379-383.

Chen, et al. Tributyrin: a prodrug of butyric acid for potential clinical application in differentiation therapy. Cancer Research. Jul. 1, 1994;54:3494-3499. 0.

Cheng, et al. Functional activation of the cystic fibrosis trafficking mutant .DELTA.F508-CFTR by expression. Am. J. Physiol. 1995;268:L615-24.

Chu, et al. In situ detection of Epstein-Barr virus in breast cancer. Cancer Lett. 1998;124:53-57.

Chung, et al. A novel approach for nasopharyngeal carcinoma treatment uses phenylbutyrate as a protein kinase C modulator: implications for radiosensitization and EBV-targeted therapy. Clin Cancer Res. Apr. 2000;6(4):1452-8.

(56) References Cited

OTHER PUBLICATIONS

Clegg, et al. Abnormal human haemoglobins. Separation and characterization of the alpha and beta chains by chromatography, and the determination of two new variants, hb Chesapeak and hb J (Bangkok). J Mol Biol. Aug. 1966;19(1):91-108.
Coates, et al. Persistence of Epstein-Barr virus in Reed-Sternberg cells throughout the course of Hodgkin's disease. J Pathol. 1991;164:291-291.
Colombo. Natural history and pathogenesis of hepatitis C virus related hepatocellular carcinoma. Journal of Hepatology. 1999;31:(1):25-30. Suppl.
Constantaoulakis, et al. On the induction of fetal hemogloving by butyrates: in vivo and in vitro studies with sodium butyrate and comparison of combination treatments with 5-AzaC. Blood. Nov. 1, 1989;74(6):1963-1971.
Cook, et al. Effect of sodium butyrate on α-Fetoprotein gene expression in rat hepatoma cells in vitro. Cancer Research. Jul. 1985;45:3215-3219.
Copeland, et al. Mast cell growth factor maps near the steel locus on mouse chromosome 10 and is deleted in a Number of steel alleles. Cell. Oct. 5, 1990;63:175-183.
Cossman, et al. Induction of differentiation in a case of common acute lymphoblastic leukemia. The New England Journal of Medicine. Nov. 11, 1982;307(20):1251-54.
Countryman et al., Histone hyperacetylation occurs on promoters of lytic cycle regulatory genes in Epstein-Barr virus-infected cell lines which are refractory to disruption of latency by histone deacetylase inhibitors. Journal of Virology. 82(10):4706-4719 (2008).
Curtis, et al. Risk of lymphoproliferative disorders after bone marrow transplantation: A multi-institutional study. Blood. 1999;94:2208-2216.
Dakshinamurty, et al. Ternary liquid equilibrium systems ethanol-water-methyl isobutyl carbinol and acetic acid-water-ethyl butyrate. J. Chem. Eng. Data. 1972;17(3):379-383.
Daniel. Pharmacokinetic study of butyric acid administered in vivo as sodium and arginine butyrate salts. Clinica Chimica Acta. 1989;181:255-264.
Dantchev,et al. Behavior of certain pyrimidine compounds of fumeric acid, and of malic acid with regard to the protection of red blood cells of the rabbit intoxicated with phenylhydrazine. Comportement de certain composés pyrimidiques, de 1' acidew fumarique et de 1' acide maléique â 1' égard de las protection des globules rouges du lapin intoxiqut par la phénylhydrazine C.R. Acad. Sci. Hebd. Sceances Acad. Sci. D. Mar. 1967;264(11):1467-1470. (in French with English abstract).
De Bruin, et al. Detection of Epstein-Barr virus nucleic acid sequences and protein in nodal T-cell lymphomas: relation between latent membrane protein I positively and clinical course. Histopathology. 1993;23:509-509.
De Bruin, et al. Presence of Epstein-Barr virus in extranodal T-cell lymphomas: differences in relation to site. Blood. 1994;83(10):1612-1612.
De Vente, et al. Effects of adenosine and adenosine-analogs on adenylate cyclase activity in the rat adipocyte plasma membrane: comparison of the properties of the enzyme with Mn2* and Mg2+ as divalent cations. Molecular and Cellular Biology. 1981;40:65-73.
Dimaio, et al. Directed enzyme pro-drug gene therapy for pancreatic cancer in vivo. Surgery. Aug. 1994;116(2):205-13.
Dokmanovic, et al. Histone deacetylase inhibitors: overview and perspectives. Mol Cancer Res. Oct. 2007;5(10):981-9.
Donaldson, et al. Cytotoxicity of the anticancer agents cisplatin and taxol during cell proliferation and the cell cycle. Int J Cancer. Jun. 15, 1994;57(6):847-55.
Douillard, et al. Phase I trial of interleukin 2 (IL2) and arginine butyrate (ArgB) in metastatic colorectal cancer. Proc. Am. Assn. for Cancer Research. 1998;39:606. (Abstract only).
Egorin, et al. Phase 1 clinical and pharmacokinetic study of hexamethylene bisacetamide (NSC 95580) administered as a five-day continuous infusion. Cancer. Res. 1987;47:617-623.

Elaut, et al. The pharmaceutical potential of histone deacetylase inhibitors. Curr Pharm Des. 2007;13(25):2584-620.
Ellis, et al. Synthetic human β-globin 5'HS2 constructs function as locus control regions only in multicopy transgene concatamers. EMBO Journal. 1993;12:127-134.
El-Nawawy, et al. Organic pesticides. II. (Arylthio) acetic acids, (arylenedithio) diacetic acids, and several of their S-alkylisothiuronium salts. Alexandria J. Agr. Res. 1970;16(2):173-184, (Abstract only).
Endo, et al. Differential induction of adult and fetal globin gene expression in the human CML cell subline KU-812F/33. J. Biochem. 1994;115:540-544. 1994
Evans, et al. A population-based case-control study of EBV and other viral antibodies among persons with Hodgkin's disease and their siblings. Int J Cancer. 1984;34:149-149.
Faller, et al. Arginine butyrate-induced susceptibility to ganciclovir in an Epstein-Barr Virus (EBV) associated lymphona. Am. Soc. Of Hematology [Blood]. 1995;86(10)(1):342a.
Faller, et al. Arginine Butyrate-induced susceptibility to ganciclovir in Epstein-Barr virus (EBV)-associated lymphomas. Proceedings of the American Association for Cancer Research. 1996;37:411-412.
Faller, et al. Phase I/II trial of arginne butyrate to induce viral TK gene expression in Epstein-Barr Virus (EBV)-associated lymphomas. Proc. Am. Assn. For Cancer Research. Mar. 2000;41:544. (Abstract only).
Faucitano, et al. Reaction of gases with irradiated organic solids. I. Preliminary results on propionamide, n-butyramide, and isobutyramide. Ric. Sci. 1967;37(12):1149-1155. (Abstract only).
Feng et al., Valproic acid enhances the efficacy of chemotherapy in EBV-positive tumors by increasing lytic viral gene expression. Cancer Res. 66(17):8762-8769 (2006).
Flyer, et al. Retrovirus-induced changes in major histocompatibility complex antigen expression influence susceptibility to lysis by cytotoxic T lymphocytes. The Journal of Immunology. Oct. 1985;135(4):2287-92.
Forrester, et al. Molecular analysis of the human β-globin locus activation region. Proc. Natl. Acad. Sci. USA. 1989;86:5439-5443.
Foss, et al. Biomodulatory effects of butyric acid derivatives on leukemia and lymphoma cells. Blood. 1993; 82/10 Suppl. 1:564A. (1993) The American Society of Hematology, 35th Annual Meeting, Dec 3-7, Abstract only.
Franke, et al. Experiences with alpha-aminoisobutyric acid in the treatment of wounds. Zentralbl Chir. 1954;79(18):769-76.
Fraser, et al. Each hypersensitive site of the human β-globin locus control region confers a different developmental pattern of expression on the globin genes. Genes Dev. 1993;7:106-13.
Garre, et al. Regulation of acetylcholinesterase expression in the K-562 cell line. Cancer Research. Sep. 1984;44:3749-3751.
Garsetti, et al. Butyric acid-induced differentiation of HL-60 cells increases the expression of a single lysophospholipase. Biochem. J. 1992;288:831-837.
Gaudet, et al. Differential regulation of arylamine and arylalkylamine N-acetyltransferases in human retinoblastoma (Y-79) cells. Neurochem Int. 1993;22(3):271-275.
Gerharz, et al. Modulation of invasive potential in different clonal subpopulations of a rat rhabdomyosarcoma cell line (BA-HAN-1) by differentiation induction. Clin. Exp. Metastasis. 1993;11(1):55-67.
Ghanayem, et al. Structure-activity relationships for the in vitro hematotoxicity of N-alkoxyacetic acids, the toxic metabolites of glycol ethers. Chem.-Biol. Interactions. 1989;70:339-352.
Ghosh et al., Histone deacetylase inhibitors are potent inducers of gene expression in latent EBV and sensitize lymphoma cells to nucleoside antiviral agents. Blood. 119(4): 1008-1017 (2012).
Ghosh, et al. Short, discontinuous exposure to butyrate effectively sensitizes latently EBV-infected lymphoma cells to nucleoside analogue antiviral agents. Blood Cells Mol Dis. Jan.-Feb. 2007;38(1):57-65. Epub Dec. 11, 2006.
Gilbert, et al. A phase I dose escalation and bioavailability study of oral sodium phenylbutyrate in patients with refractory solid tumor malignancies. Clin Cancer Res. Aug. 2001;7(8):2292-300.
Ginder, et al. Activiation of a chicken embryonic globin gene in adult erythroid cells by 5-Azacytidine and sodium butyrate. Proc. Natl. Acad. Science, USA. Jul. 1984;81:3954-3958.

(56) References Cited

OTHER PUBLICATIONS

Glaser, et al. Epstein-Barr virus-associated Hodgkin's disease: epidemiologic characteristics in international data. Int J Cancer. 1997;70(4):375-382.
Glaser, K. HDAC inhibitors: clinical update and mechanism-based potential. Biochem Pharmacol. Sep. 1, 2007;74(5):659-71. Epub Apr. 7, 2007.
Golub, et al. Induction of dormant HIV-1 by sodium butyrate: involvement of the TATA box in the activation of the HIV-1 promoter. AIDS. 1991;5(6):663-668.
Gradoville, et al. Protein kinase C-independent activation of the Epstein-Barr virus lytic cycle. J Virol. Jun. 2002;76(11):5612-26.
Gredmark, et al. Active cytomegalovirus replication in patients with coronary disease. Scand Cardiovasc J. Aug. 2007;41(4):230-4.
Greenspan, et al. Replication of Epstein-Barr virus within the epithelial cells of oral "hairy" leukoplakia, an AIDS-associated lesion. N Engl J Med. 1985;313:1564-1564.
Gross, et al. B cell lymphoproliferative disorders following hematopoietic stem cell transplantation. Risk factors, treatment and outcome. Bone Marrow Transplant. 1999;23:251-258.
Grufferman, et al. Hodgkin's disease in siblings. N Engl J Med. 1977;296:248-250.
Guilbaud, et al. Effects of differentiation-inducing agents on maturation of human MCF-7 breast cancer cells. Journal of Cellular Physiology. 1990;145:162-172.
Gum, et al. Effects of sodium butyrate on human colonic adenocarcinoma cells. The Journal of Biological Chemistry. Jan. 25, 1987;262(3):1092-1097.
Hahn, et al. Therapeutic outcome of Epstein-Barr virus positive T/NK cell lymphoma in the upper aerodigestive tract. Yonsei Med J. 2002;43:175-182.
Hanto, et al. Epstein-Barr virus-induced polyclonal and monoclonal B-cell lymphoproliferative diseases occurring after renal transplantation. Ann Surg. 1983;198:356-369.
Harabuchi, et al. Epstein-Barr virus in nasal T-cell lymphomas in patients with lethal midline granuloma. Lancet. 1990;335:128-128.
Harig, et al. Treatment of diversion colitis with short-chain-fatty acid irrigation. N. Engl. J. Med. 1989;320(1):23-28.
Henle, et al. Epstein-Barr virus and human malignancies. Cancer. Oct. 1974;34(4 Suppl):suppl:1368-74.
Henle et al., Relation of Burkitt's tumor-associated herpes-type virus to infectious mononucleosis. Proc Natl Acad Sci USA. 59(1):94-101 (1968).
Herbst et al., Epstein-Barr virus latent membrane protein expression in Hodgkin and Reed-Sternberg cells. Proc Natl Acad Sci USA. 88(11):476-4770 (1991).
Hierro et al., Efficacy and Safety of Valganciclovir in Liver-Transplanted Children Infected with Epstein-Barr Virus. Liver Transplantation 14: 1185-1193 (2008).
Ho, et al. Presence of Epstein-Barr virus DNA in nasal lymphomas. Hematol Oncol. 1990;8:271-271.
Hock, et al., Retrovirus-mediated transfer and express of drug resistance genes in human hematopoietic progenitor cells. Nature. Mar. 20, 1986;320:275-277.
Hoessly, et al. Factors responsible for variable reported lineages of HL-60 cells induced to mature with butyric acid. Cancer Research. Jul. 1, 1989;49:3594-97.
Hoey, et al. Molecular cloning and functional analysis of *drosophila* TAF110 reveal properties expected of coactivators. Cell. 1993;72:247-60.
Horig et al. From bench to clinic and back: Perspective on the 1st IQPC Translational Research conference. J Transl Med 2(1):44 (2004).
Hsu, et al. Epstein-Barr virus-associated malignancies: epidemiologic patterns and etiologic implications. Crit Rev Oncol Hematol. 2000;34:27-53.
Huang, et al. The hematopoietic growth factor KL is encoded by the SI locus and is the ligand of the o-kit receptor, the gene product of the W locus. Cell. Oct. 5, 1990;63:225-233.
Huber, et al. In vivo antitumor activity of 5-fluorocytosine on human colorectal carcinoma cells genetically modified to express cytosine deaminase. Cancer Res. Oct. 1, 1993;53(19):4619-26.
Huber, et al. Metabolism of 5-fluorocytosine to 5-fluorouracil in human colorectal tumor cells transduced with the cytosine deaminase gene: significant antitumor effects when only a small percentage of tumor cells express cytosine deaminase. Proc Natl Acad Sci U S A. Aug. 16, 1994;91(17):8302-6.
Hurford, et al. Gene therapy of metastatic cancer by in vivo retroviral gene targeting. Nat Genet. Aug. 1995;10(4):430-5.
Ikuta. Alterations in protein-DNA interactions in the y-globin gene promoter in response to butyrate therapy. Blood. Oct. 15, 1998;92(8);2924-33.
International Application No. PCT/US2016/038148 International Preliminary Report on Patentability dated Dec. 28, 2017.
Jaffe, et al. Classification of cytotoxic T-Cell and natural killer cell lymphomas. Semin Hematol. 2003;40:175-184.
Jiwa, et al. Epstein-Barr virus DNA in Reed-Sternberg cells of Hodgkin's disease is frequently associated with CR2 (EBV receptor) expression. Histopathology. 1992;21:51-51.
Johansson, et al. Epstein-Barr Virus (EBV)-associated antibody pattern in malignant lymphoma and leukemia. 1. Hodgkin's disease. Int J Cancer. 1970;5:450-450.
Johnson. L-carnitine for treatment of distal ulcerative colitis. Gastroenterology. Nov. 1992;103(5):1709-10.
Jones, et al. Sodium valproate in combination with ganciclovir induces lysis of EBV-infected lymphoma cells without impairing EBV-specific T-cell immunity. Int J Lab Hematol. Feb. 2010;32(1 Pt 1):e169-74. Epub Jan. 12, 2009.
Jones, et al. T-cell lymphomas containing Epstein-Barr virus DNA in patients with chronic Epstein-Barr virus infections. N Engl J Med. 1988;318(12):733-733.
Kanavaros, et al. Nasal T-cell lymphoma: a clinicopathologic entity associated with peculiar phenotype and with Epstein-Barr virus. Blood. 1983;81(10):2688-2688.
Karlsson, et al. Developmental regulation of human globin genes. Ann. Rev. Biochem. 1985;54:1071-1108.
Kawa. Epstein-Barr virus-associated disease in humans. Int J Hematol. 2000;71:108-117.
Keedy, et al. A limited group of class I histone deacetylases acts to repress human immunodeficiency virus type 1 expression. J Virol. May 2009;83(10):4749-56.
Kim, et al. Modification of thermosensitivity of HeLa cells by sodium butyrate, dibutyrl cyclic adenosine 3':5'-monophosphate, and retinoic acid. Cancer Research. Feb. 1984;44:697-702.
Kirk, et al. Arginine stimulates wound healing and immune function in elderly human beings. Surgery. Aug. 1993;114(2):155-9; discussion 160.
Kleer, et al. Detection of Epstein-Barr virus in rapidly growing fibroadenomas of the breast in immunosuppressed hosts. Modern Pathol. 2002;15(7):759-764.
Koeffler. Induction of differentiation of human acute myelogenous leukemia cells: therapeutic implications. Blood. 1983;62:709-721.
Konstan, et al. Effect of high-dose ibuprofen in patients with cystic fibrosis. New England Journal of Medicine. 1995;332(13):848-854.
Korbjuhn et al., Frequent latent Epstein-Barr virus infection of neoplastic T cells and bystander B cells in human immunodeficiency virus-negative European peripheral pleomorphic T-cell lymphomas. Blood. 82(1):217-223 (1993).
Krantis, et al. Augmentation of cysteamine-induced ulceration of rat duodenum by systemically administered g-Aminobutyric Acid (GABA). Digestive Diseases and Sciences. Aug. 1989;34(8m):1211-1216.
Kwong, et al. Natural killer cell lymphoma/leukemia: pathology and treatment. Hematol Oncol. 1997;15:71-79.
Langdon, et al. Effect of sodium butyrate and other differentiation inducers of poorly differentiated human ovarian adenocarcinoma cell lines. Cancer Research Nov. 1, 1988;48:6161-6165.
Lea, et al. Butyramide and monobutyrin: growth inhibitory and differentiating agents. Anticancer Research. 1993;13:145-149.
Leavitt, et al. Butyric acid suppression of the in vitro neoplastic state of Syrian hamster cells. Nature. Jan. 1978;271(19):262-65.
Leder, et al. Differential of erythroleukemic cells in the presence of inhibitors of DNA synthesis. Science. Jul. 14, 1975;190:893-894.

(56) References Cited

OTHER PUBLICATIONS

Lee, et al. Essential role of PKCdelta in histone deacetylase inhibitor-induced Epstein-Barr virus reactivation in nasopharyngeal carcinoma cells. J Gen Virol. Apr. 2008;89(Pt 4):878-83.

Lee, et al. The association of Epstein-Barr virus with smooth-muscle tumors occurring after organ transplantation. N Engl J Med. 1995;332:19-25.

Leoncini, et al. Epstein-Barr virus and gastric cancer: data and unanswered questions. Int J Cancer. 1993;53:898-901.

Lilbert, et al. Common vascular changes in the jugular vein of saline controls in continuous infusion studies in the beagle dog. Toxicol. Pathol. 2004;32:694-700.

Lokeshwar, et al. Enhancement of radiation response of prostatic carcinoma by taxol: therapeutic potential for late-stage malignancy. Anticancer Res. Jan.-Feb. 1995;15(1):93-8.

Magrath, et al. Breast cancer: a new Epstein-Barr virus-associated disease? J Nat Cancer Inst. 1999;91:1349-1350.

Maia, et al. Chronic, active Epstein-Barr virus infection. Curr Opin Hematol. 2000;7:59-63.

Mankidy, et al. Short-chain fatty acids induce g-globin gene expression by displacement of a HDAC3-NCoR repressor complex. Blood. 2006;108(9):3179-3186.

Mares, et al. Evaluation of gas chromatograph packings for the separation of butyric acid from serum-catalyzed hydrolysis of ethyl butyrate. Anal Biochem. Oct. 15, 1978;90(2):824-8.

Matalon, et al. The histone deacetylase inhibitor ITF2357 decreases surface CXCR4 and CCR5 expression on CD4(+) T-cells and monocytes and is superior to valproic acid for latent HIV-1 expression in vitro. Journal of Acquired Immune Deficiency Syndromes. (54)1:1-9 (2010).

Maziarz, et al. Distinct effects of interferon-g and MHC class 1 surface antigen levels on resistance of the K562 tumor cell line. Cellular Immunology. 1990;130:329-38.

Maziarz, et al. The regulation of exogenous and endogenous class I MHC genes in a human tumor cell line, K562. Molecular Immunology. 1990;27:135-142.

McCafferty et al. Inhibition of butyric acid-induced colitis in mice by 16, 16-dimethyl prostaglandin E2. Inflammation Research. Mar. 1992;36 Suppl 1:C79-81.

McCafferty, et al. Short chain fatty acid-induced colitis in mice. Int. J. Tissue React. 1989;11(4):165-168.

McClain, et al. Association of Epstein-Barr virus with leiomyosarcomas in young people with AIDS. N Engl J Med. 1995;332:12-18.

McDonagh, et al. The Upstream Region of the Human γ-globin Gene Promoter. J. Biol. Chem. 1991;266:11965-74.

Medeiros, et al. Localization of Epstein-Barr viral genomes in angiocentric immunoproliferative lesions. Am J Surg Pathol. 1992;16:439-447.

Meijer, et al. Epstein-Barr virus and human T-cell lymphomas. Seminars in Cancer Biology. Aug. 1996;7(4):191-196.

Migliaccio, et al. Influence of recombinant hematopoietins and of fetal bovine serum on the globin synthetic pattern of human BFUe. Blood. 1990;76:1150-1157.

Miller, et al. Antibodies to butyrate-inducible antigens of Kaposi's Sarcoma-associated herpesvirus to patient with HIV-1 infection. The New England J. Of Med. 1996;334(20):1292-1297.

Miller, et al. Clinical pharmacology of sodium butyrate in patients with acute leukemia. Eur J Cancer Clin Oncol. 1987;23(9):1283-1287.

Miller, et al. Toxicity of methoxyacetic acid in rats. Fundamental and Applied Toxicology. 1982; 2:158-160.

Modell, et al. Epidemiology of haemoglobin disorders in Europe: an overview. Scand J Clin Lab. 2007;67:39-70.

Moffat, et al. Discovery of 2-(6-{[(6-fluoroquinolin-2-yl)methyl]amino}bicyclo[3.1.0]hex-3-yl)-N-hydroxypyrimidine-5-carboxamide (CHR-3996), a class I selective orally active histone deacetylase inhibitor.J Med Chem. Dec. 23, 2010;53(24):8663-78. Epub Nov. 16, 2010.

Moi, et al. Synergistic enhancement of globin gene expression by activator protein-1-like proteins. Proc. Natl. Acad. Sci. USA. 1990;87:9000-9004.

Morita, et al. Effect of sodium butyrate on alkaline phosphatase in HRT-18, a human rectal cancer cell line. Cancer Research. Nov. 1982;42:4540-4545.

Mueller, et al. Hodgkin's disease and Epstein-Barr virus. Altered antibody pattern before diagnosis. N Engl J Med. 1989;320:689-689.

Mueller, et al. In vivo footprinting of a muscle specific enhancer by ligation mediated PCR. Science. 1989;246:780-786.

Nagai, et al. Studies on the synogistic action and anti-ulcerous activity of cortisone-GABOB. Arzneim-Forsch. 1971;21(1):96-97.

Naguib, et al. Effects of N,N-dimethylformanide and sodium butyrate on enzymes of pyrimidine metabolism in cultured human tumor cells. Leukemia Research. 1987;11(10):855-861.

Newman, et al., Induction of the insulin receptor and other differentiation markers by sodium butyrate in the Burkitt lymphoma cell, Raji. Biochemical and Biophysical Research Communications. May 30, 1989;161(1):101-106.

Newman, et al. Sodium n-butyrate enhancement of prostaglandin D2 antitumor efficacy. Biochemical Pharmacology. 1985;34(20):3771-3774.

Ney, et al. Tandem AP-1-binding sites within the human β-globin dominant control region function as an inducible enhancer in erythroid cells. Genes Dev. 1990;4:993-1006.

Nguyen et al., Chemical targeting of the innate antiviral response by histone deacetylase inhibitors renders refractory cancers sensitive to viral oncolysis. Proceedings of the National Academy of Science. 105(39): 14981-14986 (2008).

Niedobitek et al., Epstein-Barr virus gene expression in Hodgkin's disease. Blood. 78(6):1628-1630 (1991).

Niedobitek. The role of Epstein-Barr virus in the pathogenesis of Hodgkin's disease. Annals of Oncology. 7:S11-S17 (1996).

Novogrodsky, et al. Effect of polar organic componds on leukemic cells. Cancer. Jan. 1, 1983;51:9-14.

Nudel, et al. Different effects of chemical inducers on expression of β globin genes in murine erythroleukemia cells. Proc. Natl. Acad. Sci. USA. Mar.1977;74(3):1100-1104.

Nudelman, et al. Novel anticancer prodrugs of butyric acid. 2. J Med Chem. Feb. 21, 1992;35(4):687-94.

Oldfield, et al. Gene therapy for the treatment of brain tumors using intra-tumoral transduction with the thymidine kinase gene and intravenous ganciclovir. Hum Gene Ther. Feb. 1993;4(1):39-69.

Oliva, et al. Histone hyperacetylation can induce unfolding of the nucleosome core particle. Nuc. Acids Res. 1990;18:2739-2747.

O'Malley, et al. Adenovirus-mediated gene therapy for human head and neck squamous cell cancer in a nude mouse model. Cancer Res. Mar. 1, 1995;55(5):1080-5.

Ormandy, et al. Coordinate regulation of oestrogen and prolactin receptor expression by sodium butyrate in human breast cancer cells. Biochemical and Biophysical Research Communications. Jan. 31, 1992;182(2):740-745.

Osato, et al. Epstein-Barr virus and gastric carcinoma. Semin Cancer Biol. 1996;7:175-182.

Pace, et al. Short-chain fatty acid derivatives induce fetal globin expression and erythropoiesis in vivo. Blood. Dec. 15, 2002;100(13):4640-8.

Pagano. Epstein-Barr virus: the first human tumor virus and its role in cancer. Proc Assoc Am Physicians. 1999;111:573-580.

Parise, et al. Liquid chromatography-mass spectrometric assay for quantitation of the short-chain fatty acid, 2,2-dimethylbutyrate (NSC 741804), in rat plasma. J Chromatogr B Analyt Technol Biomed Life Sci. Feb. 1, 2008;862(1-2):168-74.

Partington, et al. Human globin gene transcription in injected xenopus cocytes: enhancement by enhancement by sodium butyrate. EMBO J. Dec. 1, 1984;3(12):2787-92.

Patel, et al. Transcriptional activation potential of normal and tumor-associated myb isoforms does not correlate with their ability to block GCSE-induced terminal differentiation of murine myeloid precursor cells. Oncogene. 1996;13:1197-1208.

(56) References Cited

OTHER PUBLICATIONS

Perez, et al. Bryostatin-1 Synergizes with Histone Deacetylase Inhibitors to Reactivate HIV-1 from Latency. Curr HIV Res. Sep. 1, 2010;8(6):418-29.
Perrine, et al. A multi-lineage oral hemokine, HQK-1002, enhances neutrophil recovery in sub-lethally irradiated mice and in baboons. Poster presented at ASH Annual Meeting and Exposition. Dec. 2009.
Perrine, et al. A phase 1,2 trial of arginine butyrate and ganciclovir in patients with Epstein-Barr virus-associated lymphoid malignancies. Blood. 2007;109(6):2571-2578.
Perrine, et al. A short-term trial of butyrate to stimulate fetal-globin-gene expression in the βglobin disorders. N. Engl. J. Med. 1993;328:81-86.
Perrine, et al. An Interleukin 2/Sodium Butyrate combination as immunotherapy for rat colon cancer peritoneal carcinomatosis. Gasteroenterology. 1994;107:1697-1708.
Perrine, et al. Butryic acid analogues augment γ globin gene expression in neonatal erthroid progenitors. Biochemical and Biophysical Research Communication. 1987;148:694-700.
Perrine, et al. Butyrate derivatives, new agents for stimulating fetal globin production in the β-globin disorders. The American Journal of Pediatric Hematology/Oncology. 1994;16(1):67-71.
Perrine, et al. Butyrate infusions in the ovine fetus delay the biologic clock for globin gene switching. Proc. Natl. Acad. Sci. USA. 1988;85:8540-8542.
Perrine, et al. Fetal globin gene inducers: novel agents & new potential. Ann N Y Acad Sci. Submitted only; not published. Date unknown:1-21.
Perrine, et al. HQK-1001 has additive HbF-inducing activity in combination with hydroxyurea & decitabine. Slides presented at ASH Annual Meeting and Exposition. Dec 2009.
Perrine, et al. Isobutyramide, an orally bioavailable butyrate analogue, stimulates fetal globin gene expression in vitro and in vivo. British Journal of Hematology. 1994:555-561.
Perrine, et al. Phase 1 clinical testing of HQK-1001, a novel oral fetal globin gene inducer. Abstract from ASH Annual Meeting and Exposition. Dec. 2008.
Planchon, et al. Differential effects of butyrate derivatives on human breast cancer cells grown as organotypic nodules in vitro and as xenografts in vivo. In Vivo. Nov.-Dec. 1992;6(6):605-10.
Planchon, et al. Morphology and intermediate filament composition of human mammary epithelial cells treated with stable butyrate derivative. Anticancer Res. Nov.-Dec. 1992;12(6B):2315-20.
Planchon, et al. New stable butyrate derivatives alter proliferation and differentiation in human mammary cells. Int J Cancer. May 30, 1991;48(3):443-9.
Pouillart, et al. Enhancement by stable butyrate derivatives of antitumor and antiviral actions of interferon. Int. J. Cancer. 1992;51:596-601.
Prasad. Butyric acid a small fatty acid with diverse biological functions. Life Sciences. 1980;27:1351-1358.
Prochownik, et al. Deregulated expression of o-myc by murine erythroleukemia cells prevents differentiation. Nature. Aug. 28, 1986;322:848-50.
Reiss, et al. Induction of tumor cell differentiation as a therapeutic approach: preclinical models for hematopoietic and solid neoplasms. Cancer Treatment Reports. Jan. 1986;70(1):201-218.
Rephaeli, et al. Anti-lekemic effect of butyrate in-vitro and in-vivo and the development of a potent butyrate prodrug. Blood. 1990;76:115a.
Reynolds. The Extra Pharmacopoeia, 29th edition, 1989:1359.
Rickinson, et al. Epstein-Barr virus. In Fields Virology, vol. 2, 3rd Ed., B. N. Fields, D. M. Knipe, and P. M. Howley, eds. Lippincott-Raven, Philadelphia. 1996:2397-2446.
Ritchie et al., Reactivation of DNA viruses in association with histone deacetylase inhibitor therapy: a case series report. Haematologica. 94(11): 1618-1622 (2009).
Rius, et al. The induction of vimentin gene expression by sodium butyrate in human promonocytic leukemia U937 cells. Experimental Cell Research. 1990;188:129-134.

Roediger, et al. Selective reduction of fatty acid oxidation in colonocytes: correlation with ulcerative colitis. Lipids. 1990;25(10):646-652.
Rowe, et al. Colonic short-chain fatty acids: fuel from the lumen? Gastroenterology. Jul. 1992;103(1):336-8.
Rowinsky, et al. Prolonged infusion of hexamethylene bisacetamide: a phase I and pharmacological study. Cancer Res. 1987;47:5788-5795.
Roychowdhury, et al. Selective efficacy of depsipeptide in a xenograft model of Epstein-Barr virus-positive lymphoproliferative disorder. J Natl Cancer Inst. Oct. 6, 2004;96(19):1447-57.
Rubenstein, et al. A pilot clinical trial of oral sodium 4-phenylbutyrate (Buphenyl) in DELTAF508-homozygous cystic fibrosis patients: Partial restoration of nasal epithelial CFTR function. American Journal of Respiratory and Critical Care Medicine. Feb. 1998;157(2):484-490.
Rubenstein, et al. In vitro pharmacologic restoration of CFTR-mediated chloride transport with sodium 4-phenylbutyrate in cystic fibrosis epithelial cells containing delta F508-CFTR. J Clin Invest. Nov. 15, 1997;100(10):2457-2465.
Sachs. Cell differentiation and bypassing of genetic defects in the suppression of malignancy. Cancer Research. 1987;47:1981-1986.
Sacktor, The epidemiology of human immunodeficiency virus-associated neurological disease in the era of highly active antiretroviral therapy. J. Neurovirol 2: 115-121 (2002).
Sadaie, et al. Induction of developmentally programmed cell death and activation of HIV by sodium butyrate. Virology. 1994;202:513-518.
Safaya, et al. Augmentation of g-globin gene promoter activity by carboxylic acids and components of the human β-glovin locus control region. Blood. Dec. 1, 1994;84(II):3929-3925.
Saito et al., "A synthetic inhibitor of histone deacetylase, MS-12-275, with marked in vivo antitumor activity against human tumors," PNAS 96:4592-4597 (1999).
Schafer et al. Failure is an option: learning from unsuccessful proof-of-concept trials. Drug Discov Today 13(21-22):913-916 (2008).
Scheppach, et al. Effect of butyrate enemas on the colonic mucosa in distal ulcerative colitis. Gastroenterology. Jul. 1992;103(1):51-6.
Scherr, et al. School contact among persons with Hodgkin's disease. Am J Epidemiol. 1984;120:29-38.
Seifter, et al. An outlier theory of cancer curability—tumor cell differentiation as a therapeutic goal. The American Journal of Medicine. Oct. 1987;83:757-60.
Shibata, et al. Epstein-Barr virus-associated non-Hodgkin's lymphoma in patients infected with the human immunodeficiency virus. Blood. 1993;91:2101-2109.
Slamon, et al. Expression of cellular oncogenes in human malignancies. Science. 1984;224:256-262.
Speck, et al. Infection of breast epithelial cells with Epstein-Barr virus via cell-to-cell contact. J Nat Cancer Inst. 2000;92:1849-1851.
Spyrou et al., Compounds of the anthracycline family of antibiotics elevate human γ-globin expression both in erythroid cultures and in a transgenic mouse model. Blood Cells Molecules and Diseases 44(2):100-6 (2009).
Su, et al. Aggressive peripheral T-cell lymphomas containing Epstein-Barr viral DNA: A clinicopathologic and molecular analysis. Blood. 1991;77:799-808.
Sutherland, et al. Induction of the expression of HLA class I antigens on K562 by interferons and sodium butyrate. Human Immunology. 1985;12:65-73.
Swinnen. Overview of posttransplant B-cell lymphoproliferative disorders. Semin Oncol. 1999;26:21-25.
Takahashi, et al. Differentiation of cultured friend leukemia cells induced by short-chain fatty acids. Gann. Oct. 1975;66:577-580.
Tang, et al. Memory of butyrate induction by the moloney murine sarcoma virus enhancer-promoter element. Biochem and Biophys Res. Comm. 1992;189(1):141-147.
Testa. Apoptotic mechanisms in the control of erythropoiesis. Leukemia. 2004;18:1176-99.
The Merck Index of Chemicals and Drugs, 7th edition, 1960:434.
Toussirot, et al. Epstein-Barr virus in autoimmune diseases. Best Practice & Research Clinical Rheumatology. 2008;22(5):883-896.

(56) References Cited

OTHER PUBLICATIONS

Tsai et al., Interplay between PKCδ and Sp1 on histone deacetylase inhibitor-mediated Epstein-Barr virus reactivation. J Virol. Mar. 2011;85(5):2373-85. Epub Dec. 15, 2010.

Tsao, et al. Differential effects of sodium butyrate, dimethyl sulfoxide, and retinoic acid on membrane-associated antigen, enzymes, and glycoproteins of human rectal adenocarcinoma cells. Cancer Research. Mar. 1982;42:1052-1058.

Tsapis et al., HDAC inhibitors induce apoptosis in glucocorticoid-resistant acute lymphatic leukemia cells despite a switch from the extrinsic to the intrinsic death pathway. The International Journal of Biochemistry & Cell Biology 39(7-8):1500-1509 ( 2007).

Volkov, et al. Cinnamic acid in analytical chemistry. X Determination of scandium as cinnamate and its separation from the rare earth elements and yttrium. Zh. Anal. Khim 1967;22(3):340-345. (Abstract only).

Walsh, et al. Combination of drug and gene delivery by gelatin nanospheres for the treatment of cystic fibrosis. Proceedings of the International Symposium on Controlled Release of Bioactive Materials, U.S., Deerfield, IL, controlled Release Soc., vol. SYMP, 24, Jun. 15, 1997:75-76.

Wasseman, et al. Different effects of sodium butyrate and dimethylsulfoxide on gamma-glutamyl transpeptidase and allcaline phosphatase activities in MCF-7 breast cancer cells. Expl. Cell Biol. 1987;55:189-193.

Watkins, et al. Choleretic effect of structural analogs of valproic acid in the rat. Res Commun Chem Pathol Pharmacol. Mar. 1983;39(3):355-66.

Watson, et al. Butyrate acid in the treatment of cancer. The Lancet. 1933:746-748.

Weiss, et al. Detection of Epstein-Barr virus in Reed-Sternberg cells of Hodgkin's disease. N Engl J Med. 1989;320(8):502-502.

Weiss, et al. Epstein-Barr viral DNA in tissues of Hodgkin's disease. Am J Pathol. 1987;129:86-86.

Weiss, et al. Epstein-Barr virus and Hodgkin's disease. A correlative in situ hybridization and polymerase chain reaction study. Am J Pathol. 1991;139:1259-1259.

Wu, et al. Detection of EBV gene expression in Reed-Sternberg cells of Hodgkin's disease. Int J Cancer. 1990;46:801-801.

Yeivin, et al. Sodium butyrate selectively induces transcription of promoters adjacent to the MoMSV viral enhancer. Gene. Jul. 15, 1992;116(2):159-64.

Young, et al. Phase I trial and clinical pharmacological evaluation of hexamethylene bisacetamide administration by ten-day continuous intravenous infusion at twenty-eight-day intervals. Cancer Res.1988;48:7304-7309.

Zhang, et al. Effect of (E)-5-(2-bromovinyl)-2'-deoxyuridine on several parameters of Epstein-Barr virus infection. J Gen Virol. Jan. 1984;65 ( Pt 1):37-46.

Zhang, et al. Strategies in developing promising histone deacetylase inhibitors. Med Res Rev. Jul. 2010;30(4):585-602.

Zituik, et al. The Silencing of .gamma.-Globin Gene Exin a .beta.-Globin Locus Yac can be Arrested by a .alpha.-Aminobutyric Acid. Abstract of ASH Annual Meeting, Seattle, Washington, Dec 1-5, 1995.

Zur Hausen, et al. EBV DNA in biopsies of Burkitt tumours and anaplastic carcinomas of the nasopharynx. Nature. 1970;228(5276):1056-1058.

METHODS OF TREATING VIRALLY ASSOCIATED CANCERS WITH HISTONE DEACETYLASE INHIBITORS

CROSS-REFERENCE

This is a Continuation of PCT International Application No. PCT/US20/34951, filed May 28, 2020, which application claims the benefit of U.S. Provisional Application Ser. No. 62/855,454 filed on May 31, 2019, both of which are incorporated herein by reference in their entirety.

SUMMARY OF THE INVENTION

Described herein are certain dosing schedules and amounts that effectively provide efficacy and prevent and manage side effects associated with treatment of histone deacetylase inhibitor (HDACi) treatment. Optionally, these schedules and dosing regimens include treatment with an antiviral agent.

Described herein, in one aspect, is a method of treating a cancer in an individual, the method comprising administering to the individual: (a) an effective amount of a histone deacetylase inhibitor (HDACi) as a viral inducing agent, wherein the HDACi is characterized by an elimination half-life of less than 30 hours; and (b) an effective amount of an antiviral drug; wherein the individual is treated according to a treatment schedule, wherein the individual is administered a lower dosage of the HDACi for at least one dose of the treatment schedule. In certain embodiments, the individual is not administered the HDACi for at least one day of the treatment schedule. In certain embodiments, the HDACi is administered orally. In certain embodiments, the HDACi is selected from the list consisting of: vorinostat, romidepsin, mocetinostat, belinostat, pracinostat, givinostat, panobinostat, CUDC-101, CDX101, chidamide, domatinostat, and nanatinostat. In certain embodiments, the HDACi inhibits activity of a class I histone deacetylase. In certain embodiments, the HDACi is characterized by an elimination half-life of less than 24 hours. In certain embodiments, the HDACi is characterized by an elimination half-life of less than 12 hours. In certain embodiments, the HDACi is characterized by an elimination half-life of less than 4 hours. In certain embodiments, the HDACi is nanatinostat. In certain embodiments, the HDACi is administered at a total daily dose from about 10 milligrams to about 40 milligrams. In certain embodiments, the HDACi is administered at a total daily dose of about 10 milligrams. In certain embodiments, the HDACi is administered at a total daily dose of about 15 milligrams. In certain embodiments, the HDACi is administered at a total daily dose of about 20 milligrams. In certain embodiments, the HDACi is administered at a total daily dose of about 25 milligrams. In certain embodiments, the HDACi is administered at a total daily dose of about 30 milligrams. In certain embodiments, the HDACi is administered once per day. In certain embodiments, the HDACi is administered twice per day. In certain embodiments, the cytotoxic activity of the antiviral agent is activated by a viral kinase. In certain embodiments, the viral kinase comprises, an Epstein-Barr virus protein kinase, an Epstein-Barr virus thymidine kinase, a human herpes virus thymidine kinase, or a human cytomegalovirus protein. In certain embodiments, the antiviral agent is selected from the list consisting of aciclovir, ganciclovir, valaciclovir, valganciclovir, and famciclovir. In certain embodiments, the antiviral agent is valganciclovir. In certain embodiments, the antiviral agent is administered at a total daily dose of 1800 milligrams. In certain embodiments, the antiviral agent is administered at a total daily dose of 900 milligrams. In certain embodiments, the antiviral agent is administered at a total daily dose of 450 milligrams. In certain embodiments, the antiviral agent is administered every day of the treatment schedule. In certain embodiments, the antiviral agent is administered orally. In certain embodiments, the individual is not administered the HDACi for at least two days of the treatment schedule. In certain embodiments, the individual is not administered the HDACi for at least three days of the treatment schedule. In certain embodiments, the individual is not administered the HDACi for at least four days of the treatment schedule. In certain embodiments, the individual is not administered the HDACi for at least five days of the treatment schedule. In certain embodiments, the treatment schedule has a duration of one week. In certain embodiments, the treatment schedule is repeated. In certain embodiments, the HDACi is administered with food or a caloric substance. In certain embodiments, the cancer is a solid tissue cancer. In certain embodiments, the solid tissue cancer is salivary gland cancer, nasopharyngeal carcinoma, head and neck cancer, gastric cancer, a colorectal cancer, breast cancer, glioblastoma, prostate cancer, renal cancer, leiomyosarcoma, pancreatic cancer, or lung cancer. In certain embodiments, the solid tissue cancer is salivary gland cancer, nasopharyngeal carcinoma, head and neck cancer, gastric cancer, a colorectal cancer, or leiomyosarcoma. In certain embodiments, the cancer is a leukemia or a lymphoma. In certain embodiments, the leukemia or lymphoma is a B cell leukemia or lymphoma. In certain embodiments, the leukemia or lymphoma is a T cell leukemia or lymphoma. In certain embodiments, the leukemia or lymphoma is non-Hodgkin's lymphoma. In certain embodiments, the leukemia or lymphoma is Hodgkin's lymphoma. In certain embodiments, the leukemia or lymphoma is a cytomegalovirus virus positive leukemia or lymphoma. In certain embodiments, the leukemia or lymphoma is an Epstein-Barr virus positive leukemia or lymphoma. In certain embodiments, the individual is afflicted with thrombocytopenia. In certain embodiments, the individual has a platelet count of less than 50,000 platelets per microliter. In certain embodiments, the individual has an elevated creatinine level. In certain embodiments, the elevated creatinine level exceeds 1.1 mg/dL for a woman or 1.3 mg/dL for a man. In certain embodiments, the individual is selected for treatment according to the treatment schedule based on the presence of thrombocytopenia. In certain embodiments, the individual is selected based on a platelet count of less than 50,000 per microliter. In certain embodiments, the individual is selected for treatment according to the treatment schedule based on the presence of an elevated creatinine level. In certain embodiments, the elevated creatinine level exceeds 1.1 mg/dL for a woman and 1.3 mg/dL for a man.

In another aspect, described herein, is a method of treating an Epstein-Barr associated lymphoma in an individual, the method comprising administering to the individual: (a) an effective amount of nanatinostat; and (b) an effective amount of valganciclovir; wherein the individual is treated according to a treatment schedule, wherein the individual is not administered the nanatinostat for at least three days of the treatment schedule.

In another aspect, described herein, is a kit comprising: (a) an HDACi as a viral inducing agent; and (b) an antiviral agent as a cytotoxic anti-cancer agent; wherein the kit comprises a plurality of oral dosage forms, the oral dosage forms comprising the HDACi and the antiviral agent co-packaged into separate oral dosage forms. In another aspect, described herein, is a kit comprising: (a) an HDACi; and (b) an antiviral agent; wherein the kit comprises a plurality of oral dosage forms, the oral dosage forms comprising the HDACi and the antiviral agent co-formulated into a single oral dosage form, wherein at least one of the plurality of oral dosage forms comprises the antiviral agent and does not comprise the HDACi. In certain embodiments, the plurality of oral dosage forms are a pill, capsule, tablet, or gel cap. In certain embodiments, the HDACi is selected from the list consisting of: vorinostat, romidepsin, mocetinostat, belinostat, pracinostat, givinostat, panobinostat, CUDC-101, CDX101, chidamide, and nanatinostat. In certain embodiments, the HDACi inhibits activity of a class I histone deacetylase. In certain embodiments, the HDACi is characterized by an elimination half-life of less than 24 hours. In certain embodiments, the HDACi is characterized by an elimination half-life of less than 12 hours. In certain embodiments, the HDACi is characterized by an elimination half-life of less than 4 hours. In certain embodiments, the HDACi is nanatinostat. In certain embodiments, the cytotoxic activity of the antiviral agent is activated by a viral kinase. In certain embodiments, the viral kinase comprises, an Epstein-Barr virus protein kinase, an Epstein-Barr virus thymidine kinase, a human herpes virus thymidine kinase, or a human cytomegalovirus protein. In certain embodiments, the antiviral agent is selected from the list consisting of aciclovir, ganciclovir, valaciclovir, valganciclovir, and famciclovir. In certain embodiments, the antiviral agent is valganciclovir. In certain embodiments, the plurality of oral dosage forms comprise about 900 mg of valganciclovir. In certain embodiments, the plurality of oral dosage forms comprise about 450 mg of valganciclovir. In certain embodiments, the plurality of oral dosage forms comprise about 20 mg of nanatinostat. In certain embodiments, the plurality of oral dosage forms comprise about 15 mg of nanatinostat. In certain embodiments, the plurality of oral dosage forms comprise about 10 mg of nanatinostat. In certain embodiments, the plurality of oral dosage forms comprise seven or a multiple thereof. In certain embodiments, one of the plurality of oral dosage forms comprises the antiviral agent and does not comprise the HDACi. In certain embodiments, two of the plurality of oral dosage forms comprises the antiviral agent and a lower dosage amount of the HDACi. In certain embodiments, two of the plurality of oral dosage forms comprises the antiviral agent and does not comprise the HDACi. In certain embodiments, three of the plurality of oral dosage forms comprises the antiviral agent and does not comprise the HDACi. In certain embodiments, four of the plurality of oral dosage forms comprises the antiviral agent and does not comprise the HDACi. In certain embodiments, five of the plurality of oral dosage forms comprises the antiviral agent and does not comprise the HDACi. In certain embodiments, the HDACi comprises nanatinostat and the antiviral agent comprise valganciclovir.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
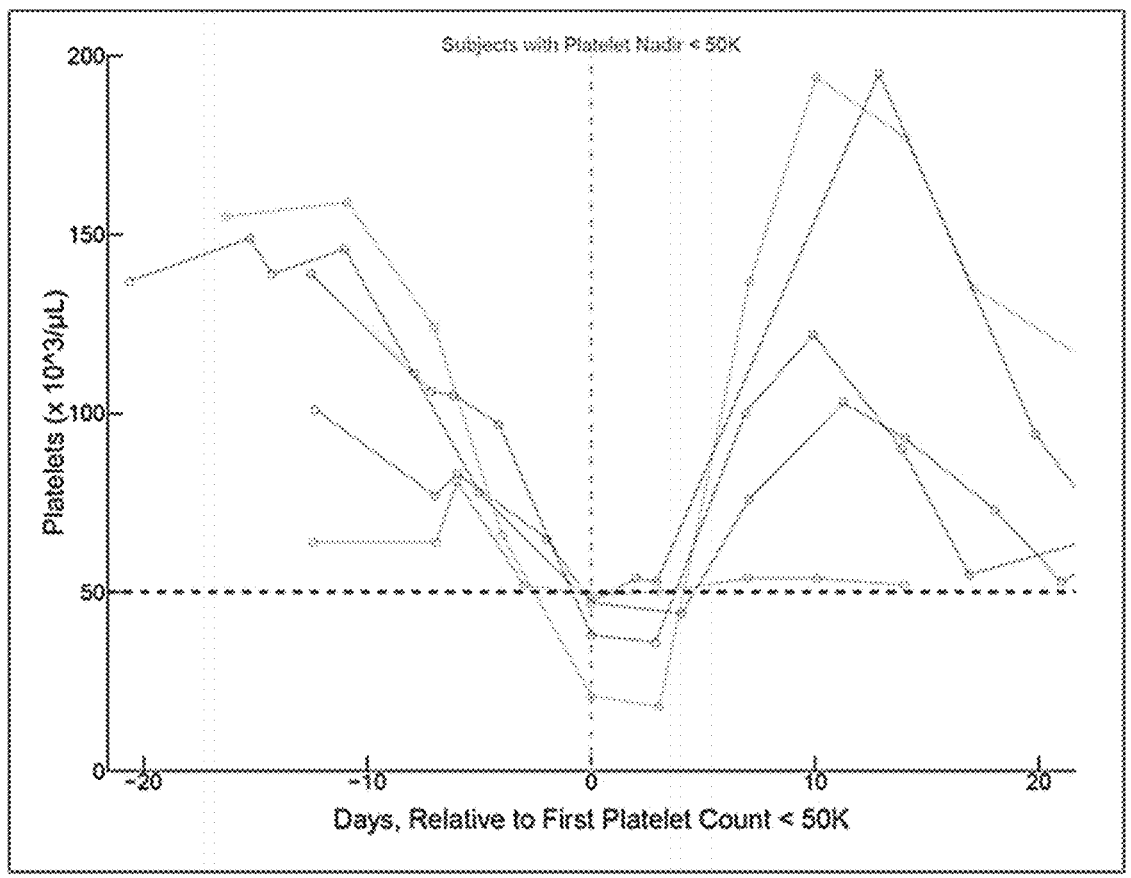
FIG. 1 illustrates rapid recovery of platelet counts in patients on nanatinostat dose hold.

There is a need for methods of treating and/or preventing viral cancers and tumors. Many patients have latent infections in which a virus is present, but is not expressing viral proteins such as viral thymidine kinase, viral protein kinase or viral polymerase, the target for common anti-viral drugs such as acyclovir, ganciclovir, and valganciclovir. A virus-inducing drug such as a histone deacetylase inhibitor (HDAC inhibitor—HDACi) can be used to induce or re-induce the expression of viral thymidine kinase, viral protein kinase, or viral polymerase in virus infected cells in the subject; the subject can then be treated with antiviral agents as cytotoxic cancer killing agents. As herpesvirus and/or other latent viral infections can be associated with a variety of cancers and or tumors, activating the latent virus with HDACi in combination with antiviral agents as a cytotoxic agent is a useful therapy in preventing or treating such conditions.

While HDACi treatment holds promise for the treatment of cancers/tumors, HDACi treatment can be associated with dose limiting toxicities that negatively influence treatment decisions, patient compliance, and patient quality of life while being treated with HDACi. Some adverse effects associated with HDACi may even limit treatment with effective therapies that employ HDACi. Disclosed herein are methods of treating patients with an HDACi that reduces side-effects associated with HDACi treatment. These methods are particularly useful for treating patients with, or avoiding hematological side effects such as thrombocytopenia, neutropenia, Leukopenia, Anemia, or Lymphopenia. These methods are also useful for treating patients with, or avoiding side effects that indicate kidney toxicity, such as elevated creatinine.

Provided herein are methods and compositions for treating viral diseases and cancers and effectively reducing side-effects, thus improving quality of life and expanding treatment options. The cancer or tumor can be associated with latent viral infections. The methods can comprise the steps of administering an HDACi to the subject. The methods can comprise the steps of administering an HDACi and an antiviral agent to the subject. The method can comprise steps of administering a viral gene inducing agent, an antiviral agent, and one or more additional agents to a subject. The methods may include the co-administration of an oral HDAC inhibitor and an antiviral agent, either in the same or separate formulations.

The methods and compositions can be used to treat and/or prevent any of the cancers described herein. Any of the HDACi and/or antiviral agents described herein can be used in the methods and compositions of the provided invention. The HDAC inhibited can be any of a class I HDAC, for instance, HDAC1, HDAC2, and HDAC3. The HDAC inhibited can be a class IIb HDAC, for instance, HDAC10. The HDAC inhibitor can be a benzamide. The benzamide can be 4SC-202. The benzamide can be chidamide (also known as CS055 or HBI-8000). The HDAC inhibitor can be selected from the list consisting of: vorinostat, romidepsin, mocetinostat, belinostat, pracinostat, givinostat, panobinostat, CUDC-101, CDX101, chidamide, domatinostat, and nanatinostat. The HDAC inhibitor can be nanatinostat.

One or more additional agents described herein can be administered to a subject. An additional agent can be selected for administration based on the type of condition the subject has or is suspected of having.

Another aspect of the present invention relates to formulations, routes of administration and effective doses for pharmaceutical compositions comprising an agent or combination of agents, e.g., HDACi, antiviral agents, or, optionally, one or more additional agents. An HDACi, antiviral agent or, optionally, one or more additional agents can be administered to a subject in separate pharmaceutical compositions or can be co-formulated in a single pharmaceutical composition. The pharmaceutical combinations can be an oral formulation. The oral formulation can be a pill, capsule, or tablet. In certain embodiments, the pill, capsule or tablet can comprise a co-formulated dose of HDACi and antiviral agent. The anti-viral agent can be a herpes, Epstein-Barr virus, or cytomegalovirus antiviral agent. In certain embodiments, the antiviral agent is selected from the list consisting of aciclovir, ganciclovir, valaciclovir, valganciclovir, and famciclovir. In certain embodiments, the antiviral agent is valganciclovir.

Described herein, in one aspect, is a method of treating a cancer in an individual, the method comprising administering to the individual: (a) an effective amount of a histone deacetylase inhibitor (HDACi), wherein the HDACi is characterized by an elimination half-life of less than 30 hours; and (b) an effective amount of an antiviral drug; wherein the individual is treated according to a treatment schedule, wherein the individual is not administered the HDACi for at least one day of the treatment schedule.

In another aspect, described herein, is a method of treating an Epstein-Barr associated lymphoma in an individual, the method comprising administering to the individual: (a) an effective amount of nanatinostat; and (b) an effective amount of valganciclovir; wherein the individual is treated according to a treatment schedule, wherein the individual is not administered the nanatinostat for at least three days of the treatment schedule.

Also provided are methods relating to dosing schedules for administering an HDACi, an antiviral agent, or, optionally, one or more additional agents. One or more pharmaceutical compositions can be administered intermittently over a period of time. The schedule can encompass intermittent administration of an HDACi, and continuous administration of an antiviral agent. The intermittent administration of the HDACi can comprise an on and an off period, for example treating with the HDACi for 1, 2, 3, 4, or 5 days in a one-week period followed by not treating with the HDACi for 6, 5, 4, 3, or 2 days. Dosage for the on period can be dose orally once a day or twice a day. Dosages applied in this type of scheme can comprise 30, mg QD, 25 mg QD, 20 mg QD, 15 m QD, 10 mg QD, 5 mg BID, 10 mg BID, or 15 mg BID.

Also described herein are kits comprising oral dosage forms formulated to reflect the on and off period, with continuous administration of the antiviral. For example, packaging with a weeks-worth or more of treatment, wherein the "on days" are oral dosage forms combining an HDACi and an antiviral, and the "off" days are oral dosage forms that comprise only the antiviral. These types of kits and packaging can increase convenience and thus compliance for patients.

In another aspect, described herein, is a kit comprising: (a) an HDACi; and (b) an antiviral agent; wherein the kit comprises a plurality of oral dosage forms, the oral dosage forms comprising the HDACi and the antiviral agent co-formulated into a single oral dosage form, wherein at least one of the plurality of oral dosage forms comprises the antiviral agent and does not comprise the HDACi.

Definitions

The terms "viral," "virus-associated," and "virally-induced" with reference to disorders are used interchangeably throughout the instant specification.

The term "obtaining" as in "obtaining the composition" is intended to include purchasing, synthesizing, or otherwise acquiring the composition (or agent(s) of the composition).

The terms "comprises", "comprising", are intended to have the broad meaning ascribed to them and can mean "includes", "including" and the like.

The term "subject", "patient" or "individual" are used interchangeably herein and refer to mammals and non-mammals, e.g., suffering from a disorder described herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, inhibiting or reducing symptoms, reducing or inhibiting severity of, reducing incidence of, prophylactic treatment of, reducing or inhibiting recurrence of, delaying onset of, delaying recurrence of, abating or ameliorating a disease or condition symptoms, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. By therapeutic benefit is meant eradication or amelioration of the underlying disorder being treated, and/or the eradication or amelioration of one or more of the physiological symptoms associated with the underlying disorder such that an improvement is observed in the patient.

Dosages are referred to herein as QD, BID or TID. QD refers to dosing once a day. BID refers to dosing twice daily of the listed dose. TID refers to dosing three times a day of the listed dose. For example, 10 mg BID refers to two 10 mg dosage units deliver daily. BID doses may be spaced apart such that they are at least about 16, 12, 10, or 8 hours apart. TID doses may be spaced at about 4, 6, or 8-hour intervals.

The terms "prevent," "preventing" or "prevention," and other grammatical equivalents as used herein, include preventing additional symptoms, preventing the underlying metabolic causes of symptoms, inhibiting the disease or condition, e.g., arresting the development of the disease or condition and are intended to include prophylaxis. The terms further include achieving a prophylactic benefit. For prophylactic benefit, the compositions are optionally administered to a patient at risk of developing a particular disease, to a patient reporting one or more of the physiological symptoms of a disease, or to a patient at risk of reoccurrence of the disease.

The terms "effective amount" or "therapeutically effective amount" as used herein, refer to a sufficient amount of at least one agent being administered which achieve a desired result, e.g., to relieve to some extent one or more symptoms of a disease or condition being treated. In certain instances, the result is a reduction and/or alleviation of the signs, symptoms, or causes of a disease, or any other desired alteration of a biological system. In certain instances, an "effective amount" for therapeutic uses is the amount of the composition comprising an agent as set forth herein required to provide a clinically significant decrease in a disease. An appropriate "effective" amount in any individual case is determined using any suitable technique, such as a dose escalation study.

The terms "administer," "administering", "administration," and the like, as used herein, refer to the methods that are used to enable delivery of agents or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Administration techniques that in some instances are employed with the agents and methods described herein include, e.g., as discussed in Goodman and Gilman, *The Pharmacological Basis of Therapeutics* (current edition), Pergamon; and Remington's, *Pharmaceutical Sciences* (current edition), Mack Publishing Co., Easton, Pa. In certain embodiments, the agents and compositions described herein are administered orally. In some embodiments, the compositions described herein are administered parenterally.

The term "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material is administered to an individual without causing significant undesirable biological effects or significantly interacting in a deleterious manner with any of the components of the composition in which it is contained.

The term "pharmaceutically acceptable excipient," as used herein, refers to carriers and vehicles that are compatible with the active ingredient (for example, a compound of the invention) of a pharmaceutical composition of the invention (and preferably capable of stabilizing it) and not deleterious to the subject to be treated. For example, solubilizing agents that form specific, more soluble complexes with the compounds of the invention can be utilized as pharmaceutical excipients for delivery of the compounds. Suitable carriers and vehicles are known to those of extraordinary skill in the art. The term "excipient" as used herein will encompass all such carriers, adjuvants, diluents, solvents, or other inactive additives. Suitable pharmaceutically acceptable excipients include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical compositions of the invention can also be sterilized and, if desired, mixed with auxiliary agents, e.g., lubricants, preservatives, stabilisers, wetting agents, emulsifiers, salts for influencing osmotic pressure, buffers, colorings, flavorings and/or aromatic substances and the like, which do not deleteriously react with the active compounds of the invention.

The invention can be understood more fully by reference to the following detailed description and illustrative examples, which are intended to exemplify non-limiting embodiments of the invention.

Herpesviruses

Herpesviruses are a large family of DNA viruses that include Herpes simplex viruses (HSVs) 1 and 2, Varicella zoster virus, Epstein-Barr virus (EBV), cytomegalovirus (CMV) and human herpesviruses (HHVs) 6A, 6B, 7 and 8, which can cause various diseases in humans. Herpesviruses have two stages of replication, the lytic and the latent. Soon after primary infection, immunological surveillance by the host force herpesviruses to enter the latent state of infection, where only a few selected genes are expressed. Conventional anti-herpesvirus drugs, such as ganciclovir, acyclovir, etc., fail to act on these latently-infected cells because the viral enzyme thymidine kinase (TK) or protein kinase (PK), which is necessary for the conversion of the prodrugs to their toxic metabolites, is not expressed in latently-infected cells. Provided herein, in some embodiments, is a combination treatment wherein lytic replication is induced and antiviral agents are administered concurrently.

For example, previous studies using patient-derived cells in vitro, and also from phase I/II clinical studies on a series of patients with EBV-associated lymphomas, have clearly shown the great promise of this combination therapy approach. Strong epidemiological association of EBV with various human lymphoid malignancies and in vitro studies demonstrating tumorigenic activity of many EBV latent gene products suggest a causal relationship between EBV and these diseases. However, as EBV maintains a latent state of infection in these lymphomas, typical anti-herpesvirus drugs, such as the nucleoside analogs ganciclovir (GCV) or acyclovir, are ineffective as these pro-drugs require expression of a lytic phase EBV protein, thymidine kinase (TK) or protein kinase (EBV-PK), for their activity. Therefore, selective induction of EBV lytic-phase gene expression in lymphoma cells that harbor latent EBV, coupled with simultaneous exposure to antiviral agents, has been advanced as promising targeted therapy, because of resulting targeting of cytotoxicity to EBV-infected tumor cells or EBV associated tumor cells.

A variety of agents including short-chain fatty acids and chemotherapeutic drugs, have been used to induce EBV lytic-phase infection in cultured cells, but these in vitro studies have generally not resulted in clinical application. For instance, arginine butyrate and GCV has been used to treat EBV-positive lymphoid malignancies in a recent Phase I/II clinical trial. In this study of 15 patients with relapsed or refractory EBV-positive lymphoid tumors, 4 patients achieved complete tumor remissions and 6 patients achieved partial tumor remissions. However, the rapid metabolism of butyrate requires continuous IV administration of high doses. Butyrate has pan-HDAC inhibitory activity, and it has been established that this activity is responsible for the induction of the EBV-TK protein. HDAC inhibitors may induce both EBV-TK and EBV-PK in EBV associated tumors. HDAC inhibitors may increase the activity of the CMV promoter in tumor cells. HDAC inhibitors may increase transcription of latent Herpes simplex virus genes in cell culture and tumors. In recent years, several potent HDAC inhibitors (HDACi) have been tested in the clinic as anti-cancer agents. In some instances, HDAC inhibitors induce lytic phase gene expression in viruses and kill virus-infected cells in combination with antiviral agents. In certain instances, HDAC inhibitors, including some new, highly-potent compounds, induce EBV lytic phase gene expression and kill EBV-infected cells in combination with antiviral agents. In some instances, HDAC inhibitors induce lytic phase gene expression in herpesviruses and kill virus-infected cells in combination with antiviral agents.

Histone Deacetylase Inhibitors

The methods of the provided invention comprise use of one or more pharmaceutical compositions provided herein comprising a histone deacetylase inhibitor (HDACi) to induce expression of a gene product in a virus-infected cell. The gene product expressed can be a viral enzyme or a cellular enzyme or activity that is largely expressed in virus-infected cells. Expression products that can be targeted include enzymes involved with DNA replication, for example, for repair or replication of the genome, assembly of complete virus particles, generation of viral membrane or walls, RNA transcription or protein translation or combinations of these activities. Interference with these processes can be performed by inducing and then acting on an enzyme and, preferably, a critical enzyme in the process.

In certain embodiments, the HDACi that can be used in conjunctions with the dosing schedules described herein is an HDACi with a short elimination half-life. In certain embodiments, the elimination half-life is less than 36 hours. In certain embodiments, the elimination half-life is less than 30 hours. In certain embodiments, the elimination half-life is less than 24 hours. In certain embodiments, the elimination half-life is less than 16 hours. In certain embodiments, the elimination half-life is less than 14 hours. In certain embodiments, the elimination half-life is less than 12 hours. In certain embodiments, the elimination half-life is less than 11 hours. In certain embodiments, the elimination half-life is less than 10 hours. In certain embodiments, the elimination half-life is less than 9 hours. In certain embodiments, the elimination half-life is less than 8 hours. In certain embodiments, the elimination half-life is less than 7 hours. In certain embodiments, the elimination half-life is less than 6 hours. In certain embodiments, the elimination half-life is less than 5 hours. In certain embodiments, the elimination half-life is between 1 and 16 hours, 1 and 14 hours, 1 and 12 hours, 1 and 11 hours, 1 and 10 hours, 1 and 9 hours, 1 and 8 hours, 1 and 7 hours, 1 and 6 hours, 1 and 5 hours, or 1 and 4 hours. In certain embodiments, the elimination half-life is less than 4 hours. In certain embodiments, the elimination half-life is between 2 and 16 hours, 2 and 14 hours, 2 and 12 hours, 2 and 11 hours, 2 and 10 hours, 2 and 9 hours, 2 and 8 hours, 2 and 7 hours, 2 and 6 hours, 2 and 5 hours, or 2 and 4 hours. In certain embodiments, the elimination half-life is between 3 and 16 hours, 3 and 14 hours, 3 and 12 hours, 3 and 11 hours, 3 and 10 hours, 3 and 9 hours, 3 and 8 hours, 3 and 7 hours, 3 and 6 hours, 3 and 5 hours, or 3 and 4 hours. In certain embodiments, the elimination half-life is between 4 and 16 hours, 4 and 14 hours, 4 and 12 hours, 4 and 11 hours, 4 and 10 hours, 4 and 9 hours, 4 and 8 hours, 4 and 7 hours, 4 and 6 hours, or 4 and 5 hours.

In some embodiments, the viral inducing agent is an HDAC inhibitor. In certain embodiments, the HDAC inhibitor is selected from the list consisting of: vorinostat, romidepsin, mocetinostat, belinostat, pracinostat, givinostat, panobinostat, CUDC-101, CDX101, chidamide, domatinostat, and nanatinostat. In certain embodiments, the HDAC inhibitor is vorinostat. In certain embodiments, the HDAC inhibitor is romidepsin. In certain embodiments, the HDAC inhibitor is mocetinostat. In certain embodiments, the HDAC inhibitor is belinostat. In certain embodiments, the HDAC inhibitor is pracinostat. In certain embodiments, the HDAC inhibitor is givinostat. In certain embodiments, the HDAC inhibitor is panobinostat. In certain embodiments, the HDAC inhibitor is CUDC-101. In certain embodiments, the HDAC inhibitor is CDX101. In certain embodiments, the HDAC inhibitor is chidamide. In certain embodiments, the HDAC inhibitor is domatinostat. In certain embodiments, the HDAC inhibitor is nanatinostat. Nanatinostat is also referred to as CHR-3996 and VRx-3996, which is chemically identical). The chemical formula of nanatinostat is 2-(((1R,5S,6s)-6-(((6-fluoroquinolin-2-yl)methyl)amino)-3-azabicyclo[3.1.0]hexan-3-yl)-N-hydroxypyrimidine-5-carboxamide. Nanatinostat is a selective Class I HDAC inhibitor and is disclosed in U.S. Pat. No. 7,932,246, which is incorporated by reference herein in its entirety.

In some embodiments, the viral inducing agent is an HDACi. In certain embodiments, the HDACi leads to Histone 3 acetylation in the peripheral blood mononuclear cells of the individual to which it is administered.

Induced Genes Including Viral-Associated Genes

HDACi (agents that induce expression) may act directly on the viral genome or indirectly through a cellular factor required for viral expression. For example, viral gene expression can be regulated through the regulation of the expression of viral transcription factors such as ZTA, RTA, tat, and tax, cellular transcription factors such as AP-1, AP-2, Sp1, NF-κB, and other transcriptional activators and/or repressors (factors), co-activators and co-repressors, histone acetylators and deacetylators, DNA methylases and demethylases, oncogenes or proto-oncogenes, or protein kinase C. These proteins act to regulate and thereby control expression of specific viral and/or other cellular genetic elements. According to the methods of the invention, control over their expression can lead to control over the infection. Other gene products, both viral and cellular in origin, whose expression can be regulated with inducing agents include proteases, polymerases, reverse transcriptases, cell-surface receptors, major histocompatibility antigens, growth factors, and combination of these products.

Additional genes whose expression or transcriptional regulation are altered in the presence of butyric acid include the oncogenes myc, ras, myb, abl and src. The activities of these gene products, as well as the activities of other oncogenes, are described in Slamon, J. D., et al. 1984 *Science* 224:256-62. Anti-proliferative activity also includes the ability to repress tumor angiogenesis through the blockade of angiogenesis factor activity, production or release, transcriptional regulation, or the ability to modulate transcription of genes under angiogenesis or growth factor or hormonal control. Either would be an effective therapy, particularly against both prostatic neoplasia and breast carcinomas. Further activities that effect transcription and/or cellular differentiation include increased intracellular cAMP levels, inhibition of histone acetylation, and inhibition of genomic methylation. Each of these activities is directly related to gene expression, and increased expression can sensitize infected cells to a specific anti-viral agent.

In other embodiments, inducing agents include HDAC inhibitors that induce EBV-PK activity (also known BGLF4) in EBV associated tumors. Expression of EBV-PK/BGLF4 sensitizes a cell to an antiviral agent. In certain instances, HDAC inhibitors induce EBV-PK. In some instances, HDAC inhibitors induce EBV-TK and/or EBV-PK. In some instances, HDAC inhibitors induce HSV-TK and/or HSV-PK. In some instances, HDAC inhibitors induce CMV-PK.

Preliminary in vitro studies according to the invention demonstrate that induction of EBV-TK activity in EBV-immortalized B-cells and patient-derived tumor cells using these drugs is possible, and that these previously resistant cells are rendered susceptible to ganciclovir therapy. Treatment of patients with viral-associated tumors such as EBV with inducing agents to induce the expression of EBV-TK/EBV-PK, and GCV, to eliminate EBV-TK/EBV-PK expressing tumor cells, is an effective, non-toxic therapy. This therapeutic regimen does not depend on the associated viral genome being the cause of the tumor. Without wishing to be bound by theory, it is believed that just the presence of the EBV genome in latent form would make the tumor susceptible to this combination protocol.

In some embodiments, an inducing agent induces viral gene expression by more than 4fold after 24 hours of treatment. In certain embodiments, an HDAC inhibitor induces TK or EBV-PK expression by more than 4-fold after 24 hours of treatment. In some embodiments, an HDAC inhibitor induces viral gene expression after about 48 hours, about 36 hours, about 24 hours, about 18 hours, about 12 hours, about 8 hours, about 6 hours, about 4 hours, about 3 hours, about 2 hours, about 1 hour, or about 30 minutes. In certain embodiments, an HDAC inhibitor induces viral gene expression in less than 48 hours, less than 36 hours, less than 24 hours, less than 18 hours, less than 12 hours, less than 8 hours, less than 6 hours, less than 4 hours, less than 3 hours, less than 2 hours, less than 1 hours, or less than 30 minutes. In some embodiments, an HDAC inhibitor induces viral gene expression in more than 48 hours, more than 36 hours, more than 24 hours, more than 18 hours, more than 12 hours, more than 8 hours, more than 6 hours, more than 4 hours, more than 3 hours, more than 2 hours, more than 1 hour, or more than 30 minutes. In certain embodiments, an HDAC inhibitor induces viral gene expression after more than 30 minutes and less than 24 hours.

Antiviral Agents

Anti-viral agents that can be used in the compositions and methods of the provided invention can include, for example, substrates and substrate analogs, inhibitors and other agents that severely impair, debilitate or otherwise destroy virus-infected cells. Substrate analogs include amino acid and nucleoside analogs. Substrates can be conjugated with toxins or other viricidal substances. Inhibitors include integrase inhibitors, protease inhibitors, polymerase inhibitors and transcriptase inhibitors such as reverse transcriptase inhibitors.

Antiviral agents that can be used in the compositions and methods of the provided invention can include, for example, ganciclovir, valganciclovir, oseltamivir (Tamiflu™), zanamivir (Relenza™), abacavir, aciclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, fusion inhibitors (e.g., enfuvirtide), ibacitabine, imunovir, idoxuridine, imiquimod, indinavir, inosine, integrase inhibitor, interferon type III, interferon type II, interferon type I, interferon, lamivudine, lopinavir, loviride, maraviroc, moroxydine, nelfinavir, nevirapine, nexavir, nucleoside analogues, peginterferon alfa-2a, penciclovir, peramivir, pleconaril, podophyllotoxin, protease inhibitor, raltegravir, reverse transcriptase inhibitor, ribavirin, rimantadine, ritonavir, pyrimidine antiviral, saquinavir, stavudine, synergistic enhancer (antiretroviral), tenofovir, tenofovir disoproxil, tipranavir, trifluridine, trizivir, tromantadine, truvada, valaciclovir (Valtrex™), vicriviroc, vidarabine, viramidine, zalcitabine, and zidovudine.

In a specific embodiment, the antiviral agent is acyclovir, ganciclovir, or valganciclovir.

In some embodiments, the antiviral agent is a nucleoside analog. Examples of nucleoside analogs include acyclovir (ACV), ganciclovir (GCV), valganciclovir, famciclovir, foscarnet, ribavirin, zalcitabine (ddC), zidovudine (AZT), stavudine (D4T), larnivudine (3TC), didanosine (ddI), cytarabine, dideoxyadenosine, edoxudine, floxuridine, idozuridine, inosine pranobex, 2'-deoxy-5-(methylamino)uridine, trifluridine and vidarabine. Examples of a few protease inhibitors that show particular promise in human therapy include saquinivir, ritonavir and indinavir. Other anti-viral agents include interferons (e.g. α-, β-, γ-interferon), cytokines such as tumor necrosis factor (TNF) or interleukins, cell receptors and growth factor antagonists, which can be purified or recombinantly produced.

In some embodiments, the antiviral agent is administered at a dose of less than 3000 mg/day. In some embodiments, the antiviral agent is administered at a dose of about 10 mg/day, about 20 mg/day, about 50 mg/day, about 100 mg/day, about 150 mg/day, about 200 mg/day, about 250 mg/day, about 300 mg/day, about 350 mg/day, about 400 mg/day, about 450 mg/day, about 500 mg/day, about 600 mg/day, about 700 mg/day, about 800 mg/day, about 900 mg/day, about 1000 mg/day, about 1200 mg/day, about 1250 mg/day, about 1400 mg/day, about 1500 mg/day, about 1600 mg/day, about 1750 mg/day, about 1800 mg/day, about 1900 mg/day, about 2000 mg/day, about 2250 mg/day, about 2500 mg/day, about 2750 mg/day, about 3000 mg/day, about 3250 mg/day, about 350 0 mg/day, about 3750 mg/day, about 4000 mg/day, about 4250 mg/day, about 4500 mg/day, about 4750 mg/day, or about 5000 mg/day. In certain embodiments, the antiviral agent is administered at a dose of less than 10 mg/day, less than 20 mg/day, less than 50 mg/day, less than 100 mg/day, less than 150 mg/day, less than 200 mg/day, less than 250 mg/day, less than 300 mg/day, less than 350 mg/day, less than 400 mg/day, less than 450 mg/day, less than 500 mg/day, less than 600 mg/day, less than 700 mg/day, less than 800 mg/day, less than 900 mg/day, less than 1000 mg/day, less than 1200 mg/day, less than 1250 mg/day, less than 1400 mg/day, less than 1500 mg/day, less than 1600 mg/day, less than 1750 mg/day, less than 1800 mg/day, less than 1900 mg/day, less than 2000 mg/day, less than 2250 mg/day, less than 2500 mg/day, less than 2750 mg/day, less than 3000 mg/day, less than 3250 mg/day, less than 3500 mg/day, less than 3750 mg/day, less than 4000 mg/day, less than 4250 mg/day, less than 4500 mg/day, less than 4750 mg/day, or less than 5000 mg/day. In some embodiments, the antiviral agent is administered at a dose of more than 10 mg/day, more than 20 mg/day, more than 50 mg/day, more than 100 mg/day, more than 150 mg/day, more than 200 mg/day, more than 250 mg/day, more than 300 mg/day, more than 350 mg/day, more than 400 mg/day, more than 450 mg/day, more than 500 mg/day, more than 600 mg/day, more than 700 mg/day, more than 800 mg/day, more than 900 mg/day, more than 1000 mg/day, more than 1200 mg/day, more than 1250 mg/day, more than 1400 mg/day, more than 1500 mg/day, more than 1600 mg/day, more than 1750 mg/day, more than 1800 mg/day, more than 1900 mg/day, more than 2000 mg/day, more than 2250 mg/day, more than 2500 mg/day, more than 2750 mg/day, more than 3000 mg/day, more than 3250 mg/day, more than 3500 mg/day, more than 3750 mg/day, more than 4000 mg/day, more than 4250 mg/day, more than 4500 mg/day, more than 4750 mg/day, or more than 5000 mg/day. In certain embodiments, the antiviral agent is administered at a dose of more than 10 mg/day and less than 5000 mg/day. In some embodiments, the antiviral agent is administered at a dose of more than 200 mg/day and less than 1000 mg/day. In certain embodiments, the antiviral agent is administered once a day (q.d, QD.), twice a day (b.i.d., BID), or thrice a day (t.i.d., TID). In some embodiments, the antiviral agent is administered daily, once a week, twice a week, three times a week, four times a week, or five times a week.

In certain embodiments, the antiviral agent is ganciclovir. In some embodiments, ganciclovir is administered at a total daily dose of 3000 mg/day. In certain embodiments, ganciclovir is administered at a dose of 1000 mg three times a day. In some embodiments, ganciclovir is administered at a dose of about 100 mg/day, about 250 mg/day, about 500 mg/day, about 750 mg/day, about 1000 mg/day, about 1500 mg/day, about 2000 mg/day, about 2500 mg/day, about 3000 mg/day, about 3500 mg/day, or about 4000 mg/day. In certain embodiments, ganciclovir is administered at a dose of less than 100 mg/day, less than 250 mg/day, less than 500 mg/day, less than 750 mg/day, less than 1000 mg/day, less than 1500 mg/day, less than 2000 mg/day, less than 2500 mg/day, less than 3000 mg/day, less than 3500 mg/day, or less than 4000 mg/day. In some embodiments, ganciclovir is administered at a dose of more than 100 mg/day, more than 250 mg/day, more than 500 mg/day, more than 750 mg/day, more than 1000 mg/day, more than 1500 mg/day, more than 2000 mg/day, more than 2500 mg/day, more than 3000 mg/day, more than 3500 mg/day, or more than 4000 mg/day. In certain embodiments, ganciclovir is administered at a dose of more than 500 mg/day and less 4000 mg/day. In some embodiments, ganciclovir is administered at a dose of more than 1000 mg/day and less than 3000 mg/day. In some embodiments, ganciclovir is administered once a day, twice a day, or three times a day. In certain embodiments, ganciclovir is administered once a week, twice a week, three times a week, four times a week, five times a week, or daily.

In some embodiments, the antiviral agent is valganciclovir. In certain embodiments, valganciclovir is administered at a total daily dose of 900 mg/day. In some embodiments, valganciclovir is administered at a dose of 900 mg once a day. In certain embodiments, valganciclovir is administered at a total daily dose of 1800 mg/day. In some embodiments, valganciclovir is administered at a dose of 900 mg twice a day.

Valganciclovir and other antivirals may be dosed at a lower level in response to certain known toxicities, such as renal or liver toxicity. Such reductions can be in accordance with label instructions. Any of the doses described herein can be reduced by 25% or 50% in response to such toxicities. In some embodiments, valganciclovir is administered at a dose of 450 mg twice a day. In some embodiments, valganciclovir is administered at a dose of 450 mg twice a day. In certain embodiments, antiviral treatment may be halted or one or more doses of a schedule may be skipped in response to renal or liver toxicity. In certain embodiments, an antiviral may not be administered for one, two, three, four, five, or six days of schedule. In certain embodiments, valganciclovir may not be administered for one, two, three, four, five, or six days of schedule. In certain embodiments the schedule is seven days.

In some embodiments, valganciclovir is administered at a dose of about 100 mg/day, about 200 mg/day, about 300 mg/day, about 400 mg/day, about 500 mg/day, about 600 mg/day, about 700 mg/day, about 800 mg/day, about 900 mg/day, about 1000 mg/day, about 1100 mg/day, about 1200 mg/day, about 1300 mg/day, about 1400 mg/day, about 1500 mg/day, about 1600 mg/day, about 1700 mg/day, about 1800 mg/day, about 1900 mg/day, or about 2000 mg/day. In certain embodiments, valganciclovir is administered at a dose of less than 100 mg/day, less than 200 mg/day, less than 300 mg/day, less than 400 mg/day, less than 500 mg/day, less than 600 mg/day, less than 700 mg/day, less than 800 mg/day, less than 900 mg/day, less than 1000 mg/day, less than 1100 mg/day, less than 1200 mg/day, less than 1300 mg/day, less than 1400 mg/day, less than 1500 mg/day, less than 1600 mg/day, less than 1700 mg/day, less than 1800 mg/day, less than 1900 mg/day, or less than 2000 mg/day. In some embodiments, valganciclovir is administered at a dose of more than 100 mg/day, more than 200 mg/day, more than 300 mg/day, more than 400 mg/day, more than 500 mg/day, more than 600 mg/day, more than 700 mg/day, more than 800 mg/day, more than 900 mg/day, more than 1000 mg/day, more than 1100 mg/day, more than 1200 mg/day, more than 1300 mg/day, more than 1400 mg/day, more than 1500 mg/day, more than 1600 mg/day, more than 1700 mg/day, more than 1800 mg/day, more than 1900 mg/day, or more than 2000 mg/day. In certain embodiments, valganciclovir is administered at a dose of more than 100 mg/day and less 2000 mg/day. In some embodiments, valganciclovir is administered at a dose of more than 500 mg/day and less than 1500 mg/day. In some embodiments, valganciclovir is administered once a day, twice a day, or three times a day. In certain embodiments, valganciclovir is administered once a week, twice a week, three times a week, four times a week, five times a week, or daily. In certain embodiments, valganciclovir is administered daily at a dose of about 900 milligrams. In certain embodiments, valganciclovir is administered daily at a dose of about 800 milligrams. In certain embodiments, valganciclovir is administered daily at a dose of about 700 milligrams. In certain embodiments, valganciclovir is administered daily at a dose of about 600 milligrams. In certain embodiments, valganciclovir is administered daily at a dose of about 500 milligrams. In certain embodiments, valganciclovir is administered daily at a dose of about 450 milligrams. In certain embodiments, valganciclovir is administered daily at a dose of about 400 milligrams. In certain embodiments, the valganciclovir is administered daily even on days when no HDACi is administered.

In certain embodiments a dosing holiday can be applied to treatment with valganciclovir. In certain embodiments, the schedule is 7 days and valganciclovir is not dosed for 1, 2, 3, 4, 5, or 6 days of the schedule. In certain embodiments, the schedule is 7 days and valganciclovir is dosed at 450 mg total daily dose on 1, 2, 3, 4, 5, or 6 days of the schedule. In certain embodiments, the schedule is 7 days and valganciclovir is dosed at 900 mg total daily dose on 1, 2, 3, 4, 5, or 6 days of the schedule.

Methods and Compositions

In one aspect, provided herein are methods for treating and/or preventing a herpesvirus associated condition. In some embodiments, the condition is associated with a latent viral infection. In certain embodiments, the herpesvirus associated condition is a cancer. In certain embodiments, the cancer is associated with infection by the Epstein-Barr virus.

In certain embodiments, the cancer is associated with infection by a Herpes simplex virus. In certain embodiments, the cancer is associated with infection by a cytomegalovirus. In certain embodiments, the methods comprise administering a viral inducing agent (e.g., an HDAC inhibitor) and an antiviral agent. In some embodiments, the methods comprise administering an HDAC inhibitor and an antiviral agent. In certain embodiments, the HDAC inhibitor and the antiviral agent are co-formulated. In some embodiments, the methods comprise administering an HDAC inhibitor and an antiviral agent. In certain embodiments, the HDAC inhibitor and the antiviral agent are formulated separately. In certain embodiments, the antiviral agent is administered daily while the HDACi is administered on only certain days. In certain embodiments, the HDACi is nanatinostat. In certain embodiments, the HDACi is administered with food or another nutritional supplement. In certain embodiments, the nanatinostat is administered with food or another nutritional supplement. In certain embodiments, the antiviral agent is not administered for 1, 2, 3, 4, 5, 6, or 7 days of the dosage schedule.

In certain embodiments, HDACi is administered at a total daily dose of about 5 milligrams to about 50 milligrams. In certain embodiments, HDACi is administered at a total daily dose of about 5 milligrams to about 10 milligrams, about 5 milligrams to about 15 milligrams, about 5 milligrams to about 20 milligrams, about 5 milligrams to about 25 milligrams, about 5 milligrams to about 30 milligrams, about 5 milligrams to about 35 milligrams, about 5 milligrams to about 40 milligrams, about 5 milligrams to about 45 milligrams, about 5 milligrams to about 50 milligrams, about 10 milligrams to about 15 milligrams, about 10 milligrams to about 20 milligrams, about 10 milligrams to about 25 milligrams, about 10 milligrams to about 30 milligrams, about 10 milligrams to about 35 milligrams, about 10 milligrams to about 40 milligrams, about 10 milligrams to about 45 milligrams, about 10 milligrams to about 50 milligrams, about 15 milligrams to about 20 milligrams, about 15 milligrams to about 25 milligrams, about 15 milligrams to about 30 milligrams, about 15 milligrams to about 35 milligrams, about 15 milligrams to about 40 milligrams, about 15 milligrams to about 45 milligrams, about 15 milligrams to about 50 milligrams, about 20 milligrams to about 25 milligrams, about 20 milligrams to about 30 milligrams, about 20 milligrams to about 35 milligrams, about 20 milligrams to about 40 milligrams, about 20 milligrams to about 45 milligrams, about 20 milligrams to about 50 milligrams, about 25 milligrams to about 30 milligrams, about 25 milligrams to about 35 milligrams, about 25 milligrams to about 40 milligrams, about 25 milligrams to about 45 milligrams, about 25 milligrams to about 50 milligrams, about 30 milligrams to about 35 milligrams, about 30 milligrams to about 40 milligrams, about 30 milligrams to about 45 milligrams, about 30 milligrams to about 50 milligrams, about 35 milligrams to about 40 milligrams, about 35 milligrams to about 45 milligrams, about 35 milligrams to about 50 milligrams, about 40 milligrams to about 45 milligrams, about 40 milligrams to about 50 milligrams, or about 45 milligrams to about 50 milligrams. In certain embodiments, HDACi is administered at a total daily dose of about 5 milligrams, about 10 milligrams, about 15 milligrams, about 20 milligrams, about 25 milligrams, about 30 milligrams, about 35 milligrams, about 40 milligrams, about 45 milligrams, or about 50 milligrams. In certain embodiments, HDACi is administered at a total daily dose of at least about 5 milligrams, about 10 milligrams, about 15 milligrams, about 20 milligrams, about 25 milligrams, about 30 milligrams, about 35 milligrams, about 40 milligrams, or about 45 milligrams. In certain embodiments, HDACi is administered at a total daily dose of at most about 10 milligrams, about 15 milligrams, about 20 milligrams, about 25 milligrams, about 30 milligrams, about 35 milligrams, about 40 milligrams, about 45 milligrams, or about 50 milligrams.

In certain embodiments, nanatinostat is administered at a total daily dose of about 5 milligrams to about 50 milligrams. In certain embodiments, nanatinostat is administered at a total daily dose of about 5 milligrams to about 10 milligrams, about 5 milligrams to about 15 milligrams, about 5 milligrams to about 20 milligrams, about 5 milligrams to about 25 milligrams, about 5 milligrams to about 30 milligrams, about 5 milligrams to about 35 milligrams, about 5 milligrams to about 40 milligrams, about 5 milligrams to about 45 milligrams, about 5 milligrams to about 50 milligrams, about 10 milligrams to about 15 milligrams, about 10 milligrams to about 20 milligrams, about 10 milligrams to about 25 milligrams, about 10 milligrams to about 30 milligrams, about 10 milligrams to about 35 milligrams, about 10 milligrams to about 40 milligrams, about 10 milligrams to about 45 milligrams, about 10 milligrams to about 50 milligrams, about 15 milligrams to about 20 milligrams, about 15 milligrams to about 25 milligrams, about 15 milligrams to about 30 milligrams, about 15 milligrams to about 35 milligrams, about 15 milligrams to about 40 milligrams, about 15 milligrams to about 45 milligrams, about 15 milligrams to about 50 milligrams, about 20 milligrams to about 25 milligrams, about 20 milligrams to about 30 milligrams, about 20 milligrams to about 35 milligrams, about 20 milligrams to about 40 milligrams, about 20 milligrams to about 45 milligrams, about 20 milligrams to about 50 milligrams, about 25 milligrams to about 30 milligrams, about 25 milligrams to about 35 milligrams, about 25 milligrams to about 40 milligrams, about 25 milligrams to about 45 milligrams, about 25 milligrams to about 50 milligrams, about 30 milligrams to about 35 milligrams, about 30 milligrams to about 40 milligrams, about 30 milligrams to about 45 milligrams, about 30 milligrams to about 50 milligrams, about 35 milligrams to about 40 milligrams, about 35 milligrams to about 45 milligrams, about 35 milligrams to about 50 milligrams, about 40 milligrams to about 45 milligrams, about 40 milligrams to about 50 milligrams, or about 45 milligrams to about 50 milligrams. In certain embodiments, nanatinostat is administered at a total daily dose of about 5 milligrams, about 10 milligrams, about 15 milligrams, about 20 milligrams, about 25 milligrams, about 30 milligrams, about 35 milligrams, about 40 milligrams, about 45 milligrams, or about 50 milligrams. In certain embodiments, nanatinostat is administered at a total daily dose of at least about 5 milligrams, about 10 milligrams, about 15 milligrams, about 20 milligrams, about 25 milligrams, about 30 milligrams, about 35 milligrams, about 40 milligrams, or about 45 milligrams. In certain embodiments, nanatinostat is administered at a total daily dose of at most about 10 milligrams, about 15 milligrams, about 20 milligrams, about 25 milligrams, about 30 milligrams, about 35 milligrams, about 40 milligrams, about 45 milligrams, or about 50 milligrams.

In some embodiments, the compositions, HDACi, or antivirals are administered on schedule in an intermittent manner. In certain embodiments, this allows for a "dose holiday" a "dose-hold" or a "structured treatment interruption," which allows for the management of negative side-effects. Suitable schedules may include a total duration of a calendar week (e.g., 7 days) or any multiple thereof according to the methods described herein. In certain embodiments, the HDACi and anti-viral agent are administered for at least one, two, three, four, five, or six days, of schedule, and no dosage amount or a reduced dosage amount of HDACi is administered for one, two, three, four, five, or six days of the schedule. In certain embodiments, the HDACi and anti-viral agent are administered on a 7-day schedule for at least one, two, three, four, five, or six days, of schedule, and no dosage amount or a reduced dosage amount of HDACi is administered for one, two, three, four, five, or six days of the schedule. In certain embodiments, the schedule is a week, and is repeated until a clinically suitable outcome is determined or reached. In certain embodiments, the schedule is a week, and is repeated for 1, 2, 3, 4, 5, 6, 7, 8, 9, 10 or more times. In certain embodiments, the HDACi is administered for one week followed by a week of no administration. In certain embodiments, nanatinostat is administered for one week followed by a week of no administration. In certain embodiments, the antiviral is administered on every day of the schedule.

In certain embodiments, the HDACi has an elimination half-life of less than 34 hours. In certain embodiments, the HDACi has an elimination half-life of less than 20 hours. In certain embodiments, the HDACi has an elimination half-life of less than 12 hours. In certain embodiments, the HDACi has an elimination half-life of less than 6 hours. In certain embodiments, the HDACi has an elimination half-life of less than 4 hours.

In certain embodiments, the HDACi is not detectable in the blood of a subject 48 hours after a dose is administered. In certain embodiments, the HDACi is not detectable in the blood of a subject 36 hours after a dose is administered. In certain embodiments, the HDACi is not detectable in the blood of a subject 24 hours after a dose is administered. In certain embodiments, the HDACi is not detectable in the blood of a subject 12 hours after a dose is administered. In certain embodiments, the dose is about 50, 40, 30, 20, 15, 10, or 5 milligrams.

In certain embodiments, the dose schedule is a week, and an HDACi is administered for 1 day of the dose schedule. In certain embodiments, the dose schedule is a week, and an HDACi is administered for 2 days of the dose schedule. In certain embodiments, the dose schedule is a week, and an HDACi is administered for 3 days of the dose schedule. In certain embodiments, the dose schedule is a week, and an HDACi is administered for 4 days of the dose schedule. In certain embodiments, the dose schedule is a week, and an HDACi is administered for 5 days of the dose schedule. In certain embodiments, the dose schedule is a week, and an HDACi is administered for 6 days of the dose schedule. In certain embodiments, the dose schedule is a week, and an HDACi is administered from between 1 and 6 days of the dose schedule. In certain embodiments, the dose schedule is a week, and an HDACi is administered from between 2 and 6 days of the dose schedule. In certain embodiments, the dose schedule is a week, and an HDACi is administered from between 3 and 6 days of the dose schedule. In certain embodiments, the dose schedule is a week, and an HDACi is administered from between 4 and 6 days of the dose schedule. In certain embodiments, the dose schedule is a week, and an HDACi is administered for 5 or 6 days of the dose schedule.

In certain embodiments the dose schedule is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days and an HDACi is not administered for 1, 2, 3, 4, 5, 6, 7, 8, 9, 10, 11, 12, 13, 14, 15, 16, 17, 18, 19, 20, 21, 22, 23, 24, 25, 26, 27, 28, 29 days of the schedule. In certain embodiments the HDACi is nanatinostat. In certain embodiments, the antiviral is administered on every day of the schedule, or may be reduced based on liver or kidney toxicity. In certain embodiments the antiviral is ganciclovir or valganciclovir.

In certain embodiments, the dose schedule is a week, and an HDACi is administered from between 1 and 5 days of the dose schedule. In certain embodiments, the dose schedule is a week, and an HDACi is administered from between 2 and 5 days of the dose schedule. In certain embodiments, the dose schedule is a week, and an HDACi is administered from between 3 and 5 days of the dose schedule. In certain embodiments, the dose schedule is a week, and an HDACi is administered for 4 or 5 days of the dose schedule.

In certain embodiments, the dose schedule is a week, and an HDACi is administered from between 1 and 4 days of the dose schedule. In certain embodiments, the dose schedule is a week, and an HDACi is administered from between 2 and 4 days of the dose schedule. In certain embodiments, the dose schedule is a week, and an HDACi is administered for 3 or 4 days of the dose schedule.

In certain embodiments, the HDACi is administered QD at 30 milligrams. In certain embodiments, the HDACi is administered QD at 25 milligrams. In certain embodiments, the HDACi is administered QD at 20 milligrams. In certain embodiments, the HDACi is administered QD at 15 milligrams. In certain embodiments, the HDACi is administered QD at 10 milligrams. In certain embodiments, the HDACi is administered BID at 20 milligrams. In certain embodiments, the HDACi is administered BID at 15 milligrams. In certain embodiments, the HDACi is administered BID at 10 milligrams. In certain embodiments, the HDACi is administered BID at 5 milligrams. In certain embodiments, the HDACi is administered TID at 15 milligrams. In certain embodiments, the HDACi is administered TID at 10 milligrams. In certain embodiments, the HDACi is administered TID at 5 milligrams. In certain embodiments, the HDACi is administered TID between about 5 milligrams and about 15 milligrams. In certain embodiments, an antiviral is administered daily during the schedule. In certain embodiments, the antiviral is valganciclovir, and the valganciclovir is administered at a dose of 900 milligrams or 450 milligrams.

In certain embodiments, the dose schedule is a week, and an HDACi is administered for 1 day followed by 6 days of no HDACi treatment. In certain embodiments, the dose schedule is a week, and an HDACi is administered for 2 days followed by 5 days of no HDACi treatment. In certain embodiments, the dose schedule is a week, and an HDACi is administered for 3 days followed by 4 days of no HDACi treatment. In certain embodiments, the dose schedule is a week, and an HDACi is administered for 4 days followed by 3 days of no HDACi treatment. In certain embodiments, the dose schedule is a week, and an HDACi is administered for 5 days followed by 2 days of no HDACi treatment. In certain embodiments, the dose schedule is a week, and an HDACi is administered for 6 days followed by 1 day of no HDACi treatment. In certain embodiments, the dose schedule is a week, and an HDACi is administered every other day on days 1, 2, 5, and 7. In certain embodiments, the dose schedule is a week, and an HDACi is administered every other day on days 2, 4, and 6. In certain embodiments, the HDACi has an elimination half-life of less than 34 hours. In certain embodiments, the HDACi has an elimination half-life of less than 20 hours. In certain embodiments, the HDACi has an elimination half-life of less than 12 hours. In certain embodiments, the HDACi has an elimination half-life of less than 6 hours. In certain embodiments, an antiviral is administered daily during the schedule. In certain embodiments, the antiviral is valganciclovir, and the valganciclovir is administered at a dose of 900 milligrams or 450 milligrams.

In certain embodiments, the dose schedule is a week, and nanatinostat is administered for 1 day of the dose schedule. In certain embodiments, the dose schedule is a week, and nanatinostat is administered for 2 days of the dose schedule. In certain embodiments, the dose schedule is a week, and nanatinostat is administered for 3 days of the dose schedule. In certain embodiments, the dose schedule is a week, and nanatinostat is administered for 4 days of the dose schedule. In certain embodiments, the dose schedule is a week, and nanatinostat is administered for 5 days of the dose schedule. In certain embodiments, the dose schedule is a week, and nanatinostat is administered for 6 days of the dose schedule. In certain embodiments, an antiviral is administered daily during the schedule. In certain embodiments, the antiviral is valganciclovir, and the valganciclovir is administered at a dose of 900 milligrams or 450 milligrams. In certain embodiments, the valganciclovir is not administered for 1, 2, 3, 4, 5, 6, or 7 days of a week-long schedule.

In certain embodiments, the dose schedule is a week, and nanatinostat is administered for 1 day followed by 6 days of no nanatinostat treatment. In certain embodiments, the dose schedule is a week, and nanatinostat is administered for 2 days followed by 5 days of no nanatinostat treatment. In certain embodiments, the dose schedule is a week, and nanatinostat is administered for 3 days followed by 4 days of no nanatinostat treatment. In certain embodiments, the dose schedule is a week, and nanatinostat is administered for 4 days followed by 3 days of no HDACi treatment. In certain embodiments, the dose schedule is a week, and nanatinostat is administered for 5 days followed by 2 days of no nanatinostat treatment. In certain embodiments, the dose schedule is a week, and nanatinostat is administered for 6 days followed by 1 day of no nanatinostat treatment. In certain embodiments, the dose schedule is a week, and nanatinostat is administered every other day on days 1, 2, 5, and 7. In certain embodiments, the dose schedule is a week, and nanatinostat is administered every other day on days 2, 4, and 6. In certain embodiments, the nanatinostat is administered QD and 30 milligrams. In certain embodiments, the nanatinostat is administered QD at 20 milligrams. In certain embodiments, the nanatinostat is administered QD at 15 milligrams. In certain embodiments, the nanatinostat is administered QD at 10 milligrams. In certain embodiments, the nanatinostat is administered BID at 15 milligrams. In certain embodiments, the nanatinostat is administered BID at 10 milligrams. In certain embodiments, the nanatinostat is administered BID at 5 milligrams. In certain embodiments, the nanatinostat is administered TID at 15 milligrams. In certain embodiments, the nanatinostat is administered TID at 10 milligrams. In certain embodiments, the nanatinostat is administered TID at 5 milligrams. In certain embodiments, an antiviral is administered daily during the schedule. In certain embodiments, an antiviral is not administered for one day of the treatment schedule. In certain embodiments, the antiviral is valganciclovir, and the valganciclovir is administered at a dose of 900 milligrams or 450 milligrams.

In certain embodiments, the dose schedule is a week, and nanatinostat is administered 20 mg QD for 1 day followed by 6 days of no nanatinostat treatment. In certain embodiments, the dose schedule is a week, and nanatinostat is administered 20 mg QD for 2 days followed by 5 days of no nanatinostat treatment. In certain embodiments, the dose schedule is a week, and nanatinostat is administered 20 mg QD for 3 days followed by 4 days of no nanatinostat treatment. In certain embodiments, the dose schedule is a week, and nanatinostat is administered 20 mg QD for 4 days followed by 3 days of no HDACi treatment. In certain embodiments, the dose schedule is a week, and nanatinostat is administered 20 mg QD for 5 days followed by 2 days of no nanatinostat treatment. In certain embodiments, the dose schedule is a week, and nanatinostat is administered 20 mg QD for 6 days followed by 1 day of no nanatinostat treatment. In certain embodiments, the dose schedule is a week, and nanatinostat is administered every other day on days 1, 2, 5, and 7. In certain embodiments, the dose schedule is a week, and nanatinostat is administered every other day on days 2, 4, and 6. In certain embodiments, an antiviral is administered daily during the schedule. In certain embodiments, the antiviral is valganciclovir, and the valganciclovir is administered at a dose of 900 milligrams or 450 milligrams.

In certain embodiments, the dose schedule is a week, and nanatinostat is administered 10 mg QD for 1 day followed by 6 days of no nanatinostat treatment. In certain embodiments, the dose schedule is a week, and nanatinostat is administered 10 mg QD for 2 days followed by 5 days of no nanatinostat treatment. In certain embodiments, the dose schedule is a week, and nanatinostat is administered 10 mg QD for 3 days followed by 4 days of no nanatinostat treatment. In certain embodiments, the dose schedule is a week, and nanatinostat is administered 10 mg QD for 4 days followed by 3 days of no HDACi treatment. In certain embodiments, the dose schedule is a week, and nanatinostat is administered 10 mg QD for 5 days followed by 2 days of no nanatinostat treatment. In certain embodiments, the dose schedule is a week, and nanatinostat is administered 10 mg QD for 6 days followed by 1 day of no nanatinostat treatment. In certain embodiments, the dose schedule is a week, and nanatinostat is administered every other day on days 1, 2, 5, and 7. In certain embodiments, the dose schedule is a week, and nanatinostat is administered every other day on days 2, 4, and 6. In certain embodiments, an antiviral is administered daily during the schedule. In certain embodiments, the antiviral is valganciclovir, and the valganciclovir is administered at a dose of 900 milligrams or 450 milligrams.

In certain embodiments, the dose schedule is a week, and nanatinostat is administered 10 mg BID for 1 day followed by 6 days of no nanatinostat treatment. In certain embodiments, the dose schedule is a week, and nanatinostat is administered 10 mg BID for 2 days followed by 5 days of no nanatinostat treatment. In certain embodiments, the dose schedule is a week, and nanatinostat is administered 10 mg BID for 3 days followed by 4 days of no nanatinostat treatment. In certain embodiments, the dose schedule is a week, and nanatinostat is administered 10 mg BID for 4 days followed by 3 days of no HDACi treatment. In certain embodiments, the dose schedule is a week, and nanatinostat is administered 10 mg BID for 5 days followed by 2 days of no nanatinostat treatment. In certain embodiments, the dose schedule is a week, and nanatinostat is administered 10 mg BID for 6 days followed by 1 day of no nanatinostat treatment. In certain embodiments, the dose schedule is a week, and nanatinostat is administered every other day on days 1, 2, 5, and 7. In certain embodiments, the dose schedule is a week, and nanatinostat is administered every other day on days 2, 4, and 6. In certain embodiments, an antiviral is administered daily during the schedule. In certain embodiments, an antiviral is administered at a lower dosage on certain days of the treatment schedule. In certain embodiments, the antiviral is valganciclovir, and the valganciclovir is administered at a dose of 900 milligrams or 450 milligrams.

In certain embodiments, the dose schedule is a week, and nanatinostat is administered 5 mg BID for 1 day followed by 6 days of no nanatinostat treatment. In certain embodiments, the dose schedule is a week, and nanatinostat is administered 5 mg BID for 2 days followed by 5 days of no nanatinostat treatment. In certain embodiments, the dose schedule is a week, and nanatinostat is administered 5 mg BID for 3 days followed by 4 days of no nanatinostat treatment. In certain embodiments, the dose schedule is a week, and nanatinostat is administered 5 mg BID for 4 days followed by 3 days of no HDACi treatment. In certain embodiments, the dose schedule is a week, and nanatinostat is administered 5 mg BID for 5 days followed by 2 days of no nanatinostat treatment. In certain embodiments, the dose schedule is a week, and nanatinostat is administered 5 mg BID for 6 days followed by 1 day of no nanatinostat treatment. In certain embodiments, the dose schedule is a week, and nanatinostat is administered every other day on days 1, 2, 5, and 7. In certain embodiments, the dose schedule is a week, and nanatinostat is administered every other day on days 2, 4, and 6. In certain embodiments, an antiviral is administered daily during the schedule. In certain embodiments, the antiviral is valganciclovir, and the valganciclovir is administered at a dose of 900 milligrams or 450 milligrams.

The HDACi can be given with food or a meal, or a type of nutritional supplement. In certain embodiments, nanatinostat is given with food or a meal or a type of nutritional supplement. Dosing the HDACi with food can be combined with the above-mentioned schedules to further increase the Cmax and bioavailability of the HDACi or nanatinostat.

Figure 5:
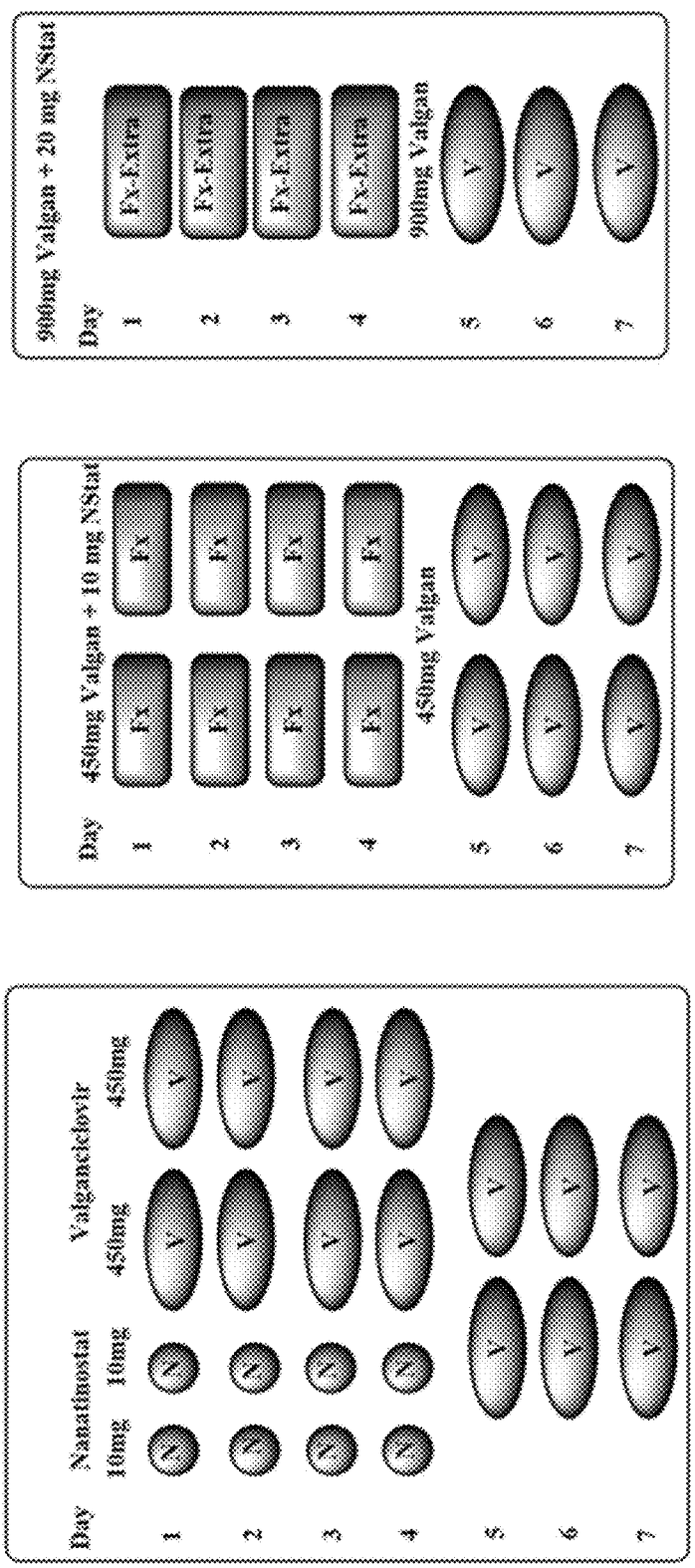
FIG. 5 illustrates non-limiting embodiments of the co-packaging and co-formulation of an HDACi and antiviral agent.

Also envisioned herein is dose packaging to efficiently and easily implement the dose schedule mentioned above. Such packaging is shown for example in FIG. 5. The packaging can be, for example, a blister pack or other sealable packing that allows the HDACi and antiviral doses for any given day to be accessed. In certain embodiments, the HDACi and antiviral agent can be packaged so that the formulations of each are separate (e.g., one day's dose comprises HDACi and antiviral agent separated. In certain embodiments, the packing can comprise co-formulated HDACi and antiviral agent. In certain embodiments, the packing can comprise co-formulated nanatinostat and valganciclovir. When such packaging is utilized with the schedules disclosed herein, a day when both HDACi and antiviral agent are to be administered the packing comprise a single oral dosage form that comprises both HDACi and antiviral agent; and a day when only an antiviral agent is to be administered the packing can comprise antiviral agent without HDACi. When such packaging is utilized with the schedules disclosed herein, a day when both nanatinostat and valganciclovir are to be administered the packing comprise a single oral dosage form that comprises both nanatinostat and valganciclovir; and a day when only valganciclovir is to be administered the packing can comprise valganciclovir without nanatinostat.

The schedules described herein can also be administered to certain patients with HDACi or antiviral side effects. In certain embodiments, the methods described herein encompass selecting a patent with thrombocytopenia. In certain embodiments, the methods and HDACi compositions described herein are for use in a patent with thrombocytopenia. Thrombocytopenia is generally defined as a platelet count below 150,000 platelets per microliter. In certain embodiments, the patient can be selected for treatment by the methods herein with a platelet count of below about 50,000; 75,000; 100,000, or 125,000 platelets per microliter. In certain embodiments, the methods do not encompass a set schedule of HDACi administration, but further monitoring for resolution of thrombocytopenia before retreatment with HDACi. In certain embodiments, if a patient has one or more dose interruptions for HDACi toxicity or has had to interrupt for more than 14 days, the methods described herein include a dose reduction for the HDACi inhibitor. In certain embodiments with a dose reduction, the HDACi will comprise nanatinostat and the dose reduction will be in 5 mg increments. In certain embodiments, the HDACi dose is re-escalated.

The schedules described herein can also be administered to certain patients with HDACi or antiviral side effects. In certain embodiments, the methods described herein encompass selecting a patent with high creatinine levels or another marker of impaired kidney function. In certain embodiments, the methods and HDACi compositions described herein are for use in a patent with high creatinine levels or another marker of impaired kidney function. A serum creatinine level that exceeds 1.1 mg/dL for a woman or 1.3 mg/dL for a man is generally considered elevated. In certain embodiments, an individual is selected to receive HDACi and antiviral according to the schedule described herein if they possess a serum creatinine level that exceeds 1.1 mg/dL for a woman or 1.3 mg/dL for a man. In certain embodiments, a patient can be selected to receive HDACi and antiviral according to the schedule described herein if they possess a blood urea nitrogen level in excess of the normal range. In certain embodiments, 20 milligrams per deciliter BUN exceeds the normal range.

The dosing schedules of HDACi and antivirals described herein can also be deployed prospectively to prevent certain side-effects in at risk individuals. In certain embodiments, a patient can be selected to receive HDACi and antiviral according to a schedule described herein if they possess a risk factor for compromised kidney function or thrombocytopenia. Risk factors for compromised kidney function comprise preexisting kidney disease, receipt of a kidney transplant, diabetes, high blood pressure, family history of kidney disease, advanced age, or African-American, Asian, Native American, or Hispanic ethnicity. Risk factors for thrombocytopenia comprise previous treatment with chemotherapy or radiation therapy, a history of anemia or thrombocytopenia.

In certain embodiments, the individual selected to be treated by the methods and schedules described herein is positive for the human immunodeficiency virus (HIV).

Types of Viruses and Virally-Induced Cancers

The methods and compositions provided herein can be used to treat and/or prevent viral associated cancers. The virus causing the infection can be a member of the herpesvirus family, a human immunodeficiency virus, parvovirus, or coxsackie virus. A member of the herpesvirus family can be herpes simplex virus, herpes genitalis virus, varicella zoster virus, Epstein-Barr virus, human herpesvirus 6, human herpesvirus 8, or cytomegalovirus. The subject can have coronary artery condition associated with a cytomegalovirus or herpes simplex virus infection. The subject can have an autoimmune condition associated with Epstein-Barr virus infection. The subject can have a lymphoma or other cancer associated with Epstein-Barr virus infection. The subject can have a lymphoma or other cancer associated with human herpesvirus 8 infection. The subject can have an autoimmune condition associated with Herpes simplex virus infection. The subject can have a cancer associate with herpes simplex virus. The subject can have an autoimmune condition associated with cytomegalovirus infection. The subject can have a lymphoma or other cancer associated with cytomegalovirus infection.

The method described herein can be used to treat a solid tumor or cancer. In certain embodiments, the solid cancer or tumor is associated with Epstein-Barr virus or cytomegalovirus. In certain embodiments, the solid cancer is salivary gland cancer, nasopharyngeal carcinoma, head and neck cancer, gastric cancer, a colorectal cancer, breast cancer, glioblastoma, prostate cancer, renal cancer, pancreatic cancer, or lung cancer. In certain embodiments, the solid tumor or cancer is herein the solid tissue cancer is salivary gland cancer, nasopharyngeal carcinoma, head and neck cancer, gastric cancer, a colorectal cancer, or leiomyosarcoma. In certain embodiments, the solid tumor or cancer is salivary gland cancer. In certain embodiments, the solid tumor or cancer is nasopharyngeal carcinoma. In certain embodiments, the solid tumor or cancer is head and neck cancer. In certain embodiments, the solid tumor or cancer is Kaposi's sarcoma. In certain embodiments, the solid tumor or cancer is gastric cancer. In certain embodiments, the solid tumor or cancer is colorectal cancer. In certain embodiments, the solid tumor or caner is positive for Epstein-Barr virus. In certain embodiments, the solid tumor or caner is positive for cytomegalovirus.

The method described herein can be used to treat a hematologic tumor or cancer. In certain embodiments, the hematologic tumor or cancer comprises leukemia or a lymphoma. In certain embodiments, the leukemia or lymphoma is associated with Epstein-Barr virus or cytomegalovirus. In certain embodiments, the hematologic cancer is leukemia or a lymphoma. In certain embodiments, the leukemia or lymphoma is a B cell leukemia or lymphoma. In certain embodiments, the leukemia or lymphoma is a T cell leukemia or lymphoma. In certain embodiments, the leukemia or lymphoma is non-Hodgkin's lymphoma. In certain embodiments, the leukemia or lymphoma is Hodgkin's lymphoma. In certain embodiments, the leukemia or lymphoma is a cytomegalovirus virus positive leukemia or lymphoma. In certain embodiments, the leukemia or lymphoma is an Epstein-Barr virus positive leukemia or lymphoma.

Formulations, Routes of Administration, and Effective Doses

Another aspect of the present invention relates to formulations, routes of administration and effective doses for pharmaceutical compositions comprising an agent or combination of agents. Such pharmaceutical compositions can be used to treat a virus-induced cancer or tumor as described above. A pharmaceutical composition can comprise a viral inducing agent. A pharmaceutical composition can comprise a viral inducing agent and one or more additional agents. A pharmaceutical composition can comprise an antiviral agent. A pharmaceutical composition can comprise an antiviral agent and one or more additional agents. A pharmaceutical composition can comprise a viral inducing agent and an antiviral agent. A pharmaceutical composition can comprise a viral inducing agent, an antiviral agent, and one or more additional agents.

The agents or their pharmaceutically acceptable salts can be provided alone or in combination with one or more other agents or with one or more other forms. For example, a formulation can comprise one or more agents in particular proportions, depending on the relative potencies of each agent and the intended indication. For example, in compositions for targeting two different targets and where potencies are similar, about a 1:1 ratio of agents can be used. The two forms can be formulated together, in the same dosage unit, e.g., in one cream, suppository, tablet, capsule, enteric coated tablet or capsule, aerosol spray, or packet of powder to be dissolved in a beverage; or each form may be formulated in a separate unit, e.g., two creams, two suppositories, two tablets, two capsules, a tablet and a liquid for dissolving the tablet, two aerosol sprays, or a packet of powder and a liquid for dissolving the powder, etc.

A "pharmaceutically acceptable salt" can be a salt that retains the biological effectiveness and properties of one or more agents, and which are not biologically or otherwise undesirable. For example, a pharmaceutically acceptable salt does not interfere with the beneficial effect of a viral inducing agent or an antiviral agent.

Salts can include those of the inorganic ions, for example, sodium, potassium, calcium, magnesium ions, and the like. Salts can include salts with inorganic or organic acids, for example, hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. If one or more agents contain a carboxy group or other acidic group, it can be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

A pharmaceutically acceptable ester or amide can be an ester or amide that retains biological effectiveness and properties of one or more agents, and which are not biologically or otherwise undesirable. For example, the ester or amide does not interfere with the beneficial effect of a viral inducing agent, an antiviral agent, or an additional agent. Esters can include, for example, ethyl, methyl, isobutyl, ethylene glycol, and the like. Amides include can include, for example, unsubstituted amides, alkyl amides, dialkyl amides, and the like.

One or more agents and/or combinations of agents can be administered with still other agents. The choice of agents that can be co-administered with the agents and/or combinations of agents can depend, at least in part, on the condition being treated. Agents of particular use in the formulations of the present invention include, for example, any agent having a therapeutic effect for a virus-induced cancer or tumor, including, e.g., drugs used to treat inflammatory conditions. For example, formulations of the instant invention can additionally contain one or more conventional anti-inflammatory drugs, such as an NSAID, e.g., ibuprofen, naproxen, acetominophen, ketoprofen, or aspirin. In some alternative embodiments, for the treatment of a virus-induced inflammatory condition can additionally contain one or more conventional influenza antiviral agents, such as amantadine, rimantadine, zanamivir, and oseltamivir. In treatments for retroviral infections, such as HIV, formulations of the instant invention may additionally contain one or more conventional antiviral drug, such as protease inhibitors (lopinavir/ritonavir {Kaletra™}, indinavir {Crixivan™}, ritonavir {Norvir™}, nelfinavir {Viracept™}, saquinavir hard gel capsules {Invirase™}, atazanavir {Reyataz™}, amprenavir {Agenerase™}, fosamprenavir {Telzir™}, tipranavir{Aptivus™}), reverse transcriptase inhibitors, includingnon-Nucleoside and Nucleoside/nucleotide inhibitors(AZT {zidovudine, Retrovir™}, ddI {didanosine, Videx™}, 3TC {lamivudine, Epivir™}, d4T {stavudine, Zerit™}, abacavir {Ziagen™}, FTC {emtricitabine, Emtriva™}, tenofovir {Viread™}, efavirenz {Sustiva™} and nevirapine {Viramune™}), fusion inhibitors T20 {enfuvirtide, Fuzeon™}, integrase inhibitors (MK-0518 and GS-9137), and maturation inhibitors (PA-457 {Bevirimat™}). As another example, formulations can additionally contain one or more supplements, such as vitamin C, E or other anti-oxidants.

One or more agents (or pharmaceutically acceptable salts, esters or amides thereof) can be administered per se or in the form of a pharmaceutical composition wherein the one or more active agent(s) is in an admixture or mixture with one or more pharmaceutically acceptable carriers. A pharmaceutical composition, as used herein, can be any composition prepared for administration to a subject. Pharmaceutical compositions can be formulated in conventional manner using one or more physiologically acceptable carriers, comprising excipients, diluents, and/or auxiliaries, e.g., that facilitate processing of the active agents into preparations that can be administered. Proper formulation can depend at least in part upon the route of administration chosen. One or more agents, or pharmaceutically acceptable salts, esters, or amides thereof, can be delivered to a patient using a number of routes or modes of administration, including oral, buccal, topical, rectal, transdermal, transmucosal, subcutaneous, intravenous, and intramuscular applications, as well as by inhalation.

For oral administration, one or more agents can be formulated readily by combining the one or more active agents with pharmaceutically acceptable carriers well known in the art. Such carriers can enable the one or more agents to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including solid diluents or fillers, sterile aqueous media and various non-toxic organic solvents. Generally, the agents of the invention can be included at concentration levels ranging from about 0.5%, about 5%, about 10%, about 20%, or about 30% to about 50%, about 60%, about 70%, about 80% or about 90% by weight of the total composition of oral dosage forms, in an amount sufficient to provide a desired unit of dosage.

Aqueous suspensions for oral use can contain one or more agents with pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like.

Oils or non-aqueous solvents can be required to bring one or more agents into solution, due to, for example, the presence of large lipophilic moieties. Alternatively, emulsions, suspensions, or other preparations, for example, liposomal preparations, can be used. With respect to liposomal preparations, any known methods for preparing liposomes for treatment of a condition can be used. See, for example, Bangham et al., *J. Mol. Biol.* 23: 238-252 (1965) and Szoka et al., *Proc. Natl Acad. Sci. USA* 75: 4194-4198 (1978), incorporated herein by reference. Ligands can also be attached to the liposomes to direct these compositions to particular sites of action. One or more agents can also be integrated into foodstuffs, e.g, cream cheese, butter, salad dressing, or ice cream to facilitate solubilization, administration, and/or compliance in certain patient populations.

Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). Disintegrating agents can be added, for example, the cross-linked polyvinyl pyrrolidone, agar, or alginic acid or a salt thereof such as sodium alginate. One or more agents can also be formulated as a sustained release preparation.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of one or more active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active agents can be dissolved or suspended in suitable liquids, such as fatty oils, liquid paraffin, or liquid polyethylene glycols. In addition, stabilizers can be added. All formulations for oral administration can be in dosages suitable for administration.

For injection, one or more agents can be formulated in aqueous solutions, including but not limited to physiologically compatible buffers such as Hank's solution, Ringer's solution, or physiological saline buffer. Such compositions can also include one or more excipients, for example, preservatives, solubilizers, fillers, lubricants, stabilizers, albumin, and the like. Methods of formulation are known in the art, for example, as disclosed in Remington's Pharmaceutical Sciences, latest edition, Mack Publishing Co., Easton P.

One or more agents can also be formulated as a depot preparation. Such long acting formulations can be administered by implantation or transcutaneous delivery (for example subcutaneously or intramuscularly), intramuscular injection or use of a transdermal patch. Thus, for example, one or more agents can be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising one or more agents can exert local and regional effects when administered topically or injected at or near particular sites of infection. Direct topical application, e.g., of a viscous liquid, gel, jelly, cream, lotion, ointment, suppository, foam, or aerosol spray, can be used for local administration, to produce, for example local and/or regional effects. Pharmaceutically appropriate vehicles for such formulation include, for example, lower aliphatic alcohols, polyglycols (e.g., glycerol or polyethylene glycol), esters of fatty acids, oils, fats, silicones, and the like. Such preparations may also include preservatives (e.g., p-hydroxybenzoic acid esters) and/or antioxidants (e.g., ascorbic acid and tocopherol). See also Dermatological Formulations: Percutaneous absorption, Barry (Ed.), Marcel Dekker Incl, 1983. In some embodiments, local/topical formulations comprising a viral inducing agent and or antiviral agent are used to treat epidermal or mucosal viral-induced inflammatory condition.

Pharmaceutical compositions can contain a cosmetically or dermatologically acceptable carrier. Such carriers can be compatible with skin, nails, mucous membranes, tissues and/or hair, and can include any conventionally used cosmetic or dermatological carrier meeting these requirements. Such carriers can be readily selected by one of ordinary skill in the art. In formulating skin ointments, an agent or combination of agents can be formulated in an oleaginous hydrocarbon base, an anhydrous absorption base, a water-in-oil absorption base, an oil-in-water water-removable base and/or a water-soluble base.

The compositions according to the present invention can be in any form suitable for topical application, including aqueous, aqueous-alcoholic or oily solutions, lotion or serum dispersions, aqueous, anhydrous or oily gels, emulsions obtained by dispersion of a fatty phase in an aqueous phase (O/W or oil in water) or, conversely, (W/O or water in oil), microemulsions or alternatively microcapsules, microparticles or lipid vesicle dispersions of ionic and/or nonionic type. These compositions can be prepared according to conventional methods. The amounts of the various constituents of the compositions according to the invention can be those conventionally used in the art. These compositions constitute protection, treatment or care creams, milks, lotions, gels or foams for the face, for the hands, for the body and/or for the mucous membranes, or for cleansing the skin. The compositions can also consist of solid preparations constituting soaps or cleansing bars.

A pharmaceutical composition can also contain adjuvants common to the cosmetic and dermatological fields, for example, hydrophilic or lipophilic gelling agents, hydrophilic or lipophilic active agents, preserving agents, antioxidants, solvents, fragrances, fillers, sunscreens, odor-absorbers and dyestuffs. The amounts of these various adjuvants can be those conventionally used in the fields considered and, for example, are from about 0.01% to about 20% of the total weight of the composition. Depending on their nature, these adjuvants can be introduced into the fatty phase, into the aqueous phase and/or into the lipid vesicles.

Ocular viral infections can be effectively treated with ophthalmic solutions, suspensions, ointments or inserts comprising an agent or combination of agents of the present invention.

In some embodiments, viral infections of the ear can be effectively treated with otic solutions, suspensions, ointments or inserts comprising an agent or combination of agents of the present invention.

One or more agents can be delivered in soluble rather than suspension form, which can allow for more rapid and quantitative absorption to the sites of action. In general, formulations such as jellies, creams, lotions, suppositories and ointments can provide an area with more extended exposure to the agents of the present invention, while formulations in solution, e.g., sprays, provide more immediate, short-term exposure.

Relating to topical/local application, a pharmaceutical composition can include one or more penetration enhancers. For example, the formulations can comprise suitable solid or gel phase carriers or excipients that increase penetration or help delivery of agents or combinations of agents of the invention across a permeability barrier, e.g., the skin. Many of these penetration-enhancing compounds are known in the art of topical formulation, and include, e.g., water, alcohols (e.g., terpenes like methanol, ethanol, 2-propanol), sulfoxides (e.g., dimethyl sulfoxide, decylmethyl sulfoxide, tetradecylmethyl sulfoxide), pyrrolidones (e.g., 2-pyrrolidone, N-methyl-2-pyrrolidone, N-(2-hydroxyethyl)pyrrolidone), laurocapram, acetone, dimethylacetamide, dimethylformamide, tetrahydrofurfuryl alcohol, L-α-amino acids, anionic, cationic, amphoteric or nonionic surfactants (e.g., isopropyl myristate and sodium lauryl sulfate), fatty acids, fatty alcohols (e.g., oleic acid), amines, amides, clofibric acid amides, hexamethylene lauramide, proteolytic enzymes, α-bisabolol, d-limonene, urea and N,N-diethyl-m-toluamide, and the like. Additional examples include humectants (e.g., urea), glycols (e.g., propylene glycol and polyethylene glycol), glycerol monolaurate, alkanes, alkanols, ORGELASE, calcium carbonate, calcium phosphate, various sugars, starches, cellulose derivatives, gelatin, and/or other polymers. A pharmaceutical composition can include one or more such penetration enhancers.

A pharmaceutical composition for local/topical application can include one or more antimicrobial preservatives, for example, quaternary ammonium compounds, organic mercurials, p-hydroxy benzoates, aromatic alcohols, chlorobutanol, and the like.

Gastrointestinal viral infections can be effectively treated with orally- or rectally delivered solutions, suspensions, ointments, enemas and/or suppositories comprising an agent or combination of agents of the present invention.

Respiratory viral infections can be effectively treated with aerosol solutions, suspensions or dry powders comprising an agent or combination of agents of the present invention. Administration by inhalation is particularly useful in treating viral infections of the lung, such as influenza. The aerosol can be administered through the respiratory system or nasal passages. For example, one skilled in the art will recognize that a composition of the present invention can be suspended or dissolved in an appropriate carrier, e.g., a pharmaceutically acceptable propellant, and administered directly into the lungs using a nasal spray or inhalant. For example, an aerosol formulation comprising a viral inducing agent and/or antiviral agent can be dissolved, suspended or emulsified in a propellant or a mixture of solvent and propellant, e.g., for administration as a nasal spray or inhalant. Aerosol formulations may contain any acceptable propellant under pressure, such as a cosmetically or dermatologically or pharmaceutically acceptable propellant, as conventionally used in the art.

An aerosol formulation for nasal administration is generally an aqueous solution designed to be administered to the nasal passages in drops or sprays. Nasal solutions can be similar to nasal secretions in that they are generally isotonic and slightly buffered to maintain a pH of about 5.5 to about 6.5, although pH values outside of this range can additionally be used. Antimicrobial agents or preservatives can also be included in the formulation.

An aerosol formulation for inhalations and inhalants can be designed so that an agent or combination of agents can be carried into the respiratory tree of the subject when administered by the nasal or oral respiratory route. Inhalation solutions can be administered, for example, by a nebulizer. Inhalations or insufflations, comprising finely powdered or liquid drugs, can be delivered to the respiratory system as a pharmaceutical aerosol of a solution or suspension of the agent or combination of agents in a propellant, e.g., to aid in disbursement. Propellants can be liquefied gases, including halocarbons, for example, fluorocarbons such as fluorinated chlorinated hydrocarbons, hydrochlorofluorocarbons, and hydrochlorocarbons, as well as hydrocarbons and hydrocarbon ethers.

Halocarbon propellants can include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarb on propellants. Halocarbon propellants are described in Johnson, U.S. Pat. No. 5,376,359, issued Dec. 27, 1994; Byron et al., U.S. Pat. No. 5,190,029, issued Mar. 2, 1993; and Purewal et al., U.S. Pat. No. 5,776,434, issued Jul. 7, 1998. Hydrocarbon propellants useful in the invention include, for example, propane, isobutane, n-butane, pentane, isopentane and neopentane. A blend of hydrocarbons can also be used as a propellant. Ether propellants include, for example, dimethyl ether as well as the ethers. An aerosol formulation of the invention can also comprise more than one propellant. For example, an aerosol formulation can comprise more than one propellant from the same class, such as two or more fluorocarbons; or more than one, more than two, more than three propellants from different classes, such as a fluorohydrocarbon and a hydrocarbon. Pharmaceutical compositions of the present invention can also be dispensed with a compressed gas, e.g., an inert gas such as carbon dioxide, nitrous oxide or nitrogen.

Aerosol formulations can also include other components, for example, ethanol, isopropanol, propylene glycol, as well as surfactants or other components such as oils and detergents. These components can serve to stabilize the formulation and/or lubricate valve components.

The aerosol formulation can be packaged under pressure and can be formulated as an aerosol using solutions, suspensions, emulsions, powders and semisolid preparations. For example, a solution aerosol formulation can comprise a solution of an agent, such as a viral inducing agent and/or antiviral agent in (substantially) pure propellant or as a mixture of propellant and solvent. The solvent can be used to dissolve the agent and/or retard the evaporation of the propellant. Solvents useful in the invention include, for example, water, ethanol and glycols. Any combination of suitable solvents can be used, optionally combined with preservatives, antioxidants, and/or other aerosol components.

An aerosol formulation can also be a dispersion or suspension. A suspension aerosol formulation may comprise a suspension of an agent or combination of agents of the instant invention, e.g., a viral inducing agent and/or antiviral agent, and a dispersing agent. Dispersing agents useful in the invention include, for example, sorbitan trioleate, oleyl alcohol, oleic acid, lecithin and corn oil. A suspension aerosol formulation can also include lubricants, preservatives, antioxidant, and/or other aerosol components.

An aerosol formulation can be formulated as an emulsion. An emulsion aerosol formulation can include, for example, an alcohol such as ethanol, a surfactant, water and a propellant, as well as an agent or combination of agents, e.g., a viral inducing agent and/or an antiviral agent. The surfactant used can be nonionic, anionic or cationic. One example of an emulsion aerosol formulation comprises, for example, ethanol, surfactant, water and propellant. Another example of an emulsion aerosol formulation comprises, for example, vegetable oil, glyceryl monostearate and propane.

Pharmaceutical compositions suitable for use in the present invention can include compositions wherein the active ingredients are present in an effective amount, i.e., in an amount effective to achieve therapeutic and/or prophylactic benefit in a host with at least one virus-induced inflammatory condition. The actual amount effective for a particular application will depend on the condition or conditions being treated, the condition of the subject, the formulation, and the route of administration, as well as other factors known to those of skill in the art. Determination of an effective amount of a viral inducing agent and/or antiviral agent is well within the capabilities of those skilled in the art, in light of the disclosure herein, and can be determined using routine optimization techniques.

An effective amount for use in humans can be determined from animal models. For example, a dose for humans can be formulated to achieve circulating, liver, topical and/or gastrointestinal concentrations that have been found to be effective in animals. One skilled in the art can determine the effective amount for human use, especially in light of the animal model experimental data described herein. Based on animal data, and other types of similar data, those skilled in the art can determine an effective amount of a composition appropriate for humans.

An effective amount when referring to an agent or combination of agents of the invention can generally mean the dose ranges, modes of administration, formulations, etc., that have been recommended or approved by any of the various regulatory or advisory organizations in the medical or pharmaceutical arts (e.g., FDA, AMA) or by the manufacturer or supplier.

Further, appropriate doses for a viral inducing agent and/or antiviral agent can be determined based on in vitro experimental results.

A person of skill in the art would be able to monitor in a patient the effect of administration of a particular agent. For example, HIV or EBV viral load levels can be determined by techniques standard in the art, such as measuring CD4 cell counts, and/or viral levels as detected by PCR. Other techniques would be apparent to one of skill in the art.

This disclosure provides for a kit, the kits can comprise one or more containers, the kit can comprise any combination of HDAC inhibitors, antivirals or additional agents mentioned in the methods of this disclosure in suitable packaging. The kit may contain instructions for use. The HDAC inhibitor or antiviral can be present in any concentration disclosed herein, can be packaged for administration by any route disclosed herein, or in any formulation disclosed herein. In some embodiments, the HDAC inhibitor and antiviral agent are packaged together, in a suitable package or container, in a kit. The kit may be for convenient administration or dosing, and management thereof. In some further embodiments, the HDAC inhibitor and antiviral are formulated together as a pharmaceutical composition in a single dose. In some alternative embodiments, the HDAC inhibitor and antiviral are formulated as separate pharmaceutical compositions. In some embodiments, the pharmaceutical composition of the HDAC inhibitor is packaged for once a week, twice a week, thrice a week, four times a week or more, once a month, twice a month, thrice a month, four times a month or more dosing; and the pharmaceutical composition of the antiviral is packaged for daily, twice daily, thrice daily, four times a day or more dosing. In some embodiments, the antiviral is administered or taken without the HDAC inhibitor. In some embodiments, the treatment course of the HDAC inhibitor and antiviral can be as follows: the HDAC inhibitor and the antiviral are taken or administered together in the same pharmaceutical composition on any of the first, second, third, fourth, fifth or more days of treatment; and the antiviral is taken or administered by itself on any of days 2, 3, 4, 5, 6, 7, 8, 9, 10, 11, 12, 13 or more. In some further embodiments, the treatment course can be as follows: the HDAC inhibitor and antiviral are taken or administered separately in different pharmaceutical composition on any of the first, second, third, fourth, fifth or more days of treatment, either at the same time or temporally separated by 1, 2, 3, 4, 5, 6, 7, 8, 9, 10, 11, 12, or more hours; and the antiviral is taken or administered by itself on any of days 2, 3, 4, 5, 6, 7, 8, 9, 10, 11, 12, 13 or more. In some embodiments, the HDAC inhibitor packaged in the kit is nanatinostat. In some embodiments, the antiviral is ganciclovir, in other embodiments, it is valganciclovir. In some embodiments, the treatment course is repeated for 1, 2, 3, 4, 5, 6, 7, 8, 9, 10, 11, 12, 13, 14 or more iterations.

The kits described herein may comprise a plurality of oral dosage forms, wherein the oral dosage form comprises an HDACi and an antiviral. In certain embodiments, the plurality comprises seven or a multiple thereof. In certain embodiments, the kit comprises one oral dosage form comprising HDACi and antiviral co-formulated into a single form, and six oral dosage forms comprising an antiviral and no or a reduced amount of HDACi. In certain embodiments, the kit comprises two oral dosage forms comprising HDACi and antiviral co-formulated into a single form, and five oral dosage forms comprising an antiviral and no or a reduced amount of HDACi. In certain embodiments, the kit comprises three oral dosage forms comprising HDACi and antiviral co-formulated into a single form, and four oral dosage forms comprising an antiviral and no or a reduced amount of HDACi. In certain embodiments, the kit comprises four oral dosage forms comprising HDACi and antiviral co-formulated into a single form, and three oral dosage forms comprising an antiviral and no or a reduced amount of HDACi. In certain embodiments, the kit comprises five oral dosage forms comprising HDACi and antiviral co-formulated into a single form, and two oral dosage forms comprising an antiviral and no or a reduced amount of HDACi. In certain embodiments, the kit comprises six oral dosage forms comprising HDACi and antiviral co-formulated into a single form, and one oral dosage form comprising an antiviral and no or a reduced amount of HDACi. The package may suitably comprise a multiple of seven of any of these amounts (e.g., kits providing one, two, or three-months' worth of dosage). The oral dosage forms may be compounded for dosing once a day, twice a day, or three times daily. In certain embodiments, the HDACi comprises nanatinostat. In certain embodiments, the amount of nanatinostat incorporated into the oral dosage form comprises 5 milligrams, 10 milligrams, 15 milligrams, 20 milligrams, 25 milligrams, 30 milligrams. In certain embodiments, the antiviral comprises valganciclovir. In certain embodiments, the amount of valganciclovir incorporated into the oral dosage form comprises 450 milligrams, 900 milligrams, or 1,800 milligrams.

The kits described herein may comprise a plurality of oral dosage forms, wherein the oral dosage form comprises an HDACi and an antiviral formulated separately. In certain embodiments, the kit comprises at least two oral dosage form comprising HDACi and antiviral formulated separately, and six oral dosage forms comprising an antiviral and no or a reduced amount of HDACi. In certain embodiments, the kit comprises four oral dosage forms comprising HDACi and antiviral formulated separately, and five oral dosage forms comprising an antiviral and no or a reduced amount of HDACi. In certain embodiments, the kit comprises six oral dosage forms comprising HDACi and antiviral formulated separately, and four oral dosage forms comprising an antiviral and no or a reduced amount of HDACi. In certain embodiments, the kit comprises eight oral dosage forms comprising HDACi and antiviral formulated separately, and three oral dosage forms comprising an antiviral and no or a reduced amount of HDACi. In certain embodiments, the kit comprises ten oral dosage forms comprising HDACi and antiviral formulated separately, and two oral dosage forms comprising an antiviral and no or a reduced amount of HDACi. In certain embodiments, the kit comprises twelve oral dosage forms comprising HDACi and antiviral formulated separately, and one oral dosage form comprising an antiviral and no or a reduced amount of HDACi. The package may suitably comprise a multiple of seven of any of these amounts (e.g., kits providing one, two, or three-months' worth of dosage). The oral dosage forms may be compounded for dosing once a day, twice a day, or three times daily. In certain embodiments, the HDACi comprises nanatinostat. In certain embodiments, the amount of nanatinostat incorporated into the oral dosage form comprises 5 milligrams, 10 milligrams, 15 milligrams, 20 milligrams, 25 milligrams, 30 milligrams. In certain embodiments, the antiviral comprises valganciclovir. In certain embodiments, the amount of valganciclovir incorporated into the oral dosage form comprises 450 milligrams, 900 milligrams, or 1,800 milligrams.

The kits of this invention are in suitable packaging. Suitable packaging includes, but is not limited to, vials, bottles, jars, flexible packaging (e.g., sealed Mylar, blister packs, plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an HDAC inhibitor. The HDAC inhibitor can be nanatinostat. The container may further comprise a second pharmaceutically active agent. This second pharmaceutically active agent can be an antiviral. The antiviral can be ganciclovir or valganciclovir.

EXAMPLES

Example 1—Clinical Trial Combining HDACi and Antiviral Treatment

Nanatinostat (Nstat) (VRx-3996 formerly known as CHR-3996) is a Class 1-selective, oral, hydroxamate histone deacetylase (HDAC) inhibitor active against HDAC 1-3 but not HDAC 6.

Ontract (NCT03397706) is a Phase 1b/2, open-label, dose-escalation (3+3 design) study followed by an expansion stage at the recommended Phase 2 dose (RP2D) of p.o. N+VG in patients with EBV-associated lymphomas. Dose schedules tested are shown in Table 1 below.

TABLE 1

Dose schedules and amounts

| Cohort | Phase 1b Escalation Dose/Schedule | |
|---|---|---|
| 1 | N 10 mg BID, daily | VG 900 mg BID |
| 2a | N 5 mg BID, daily | VG 450 mg BID |
| 2b | N 10 mg QD, daily | VG 450 mg BID |
| 2c | N 10 mg QD, daily | VG 900 mg QD |

TABLE 1-continued

Dose schedules and amounts

| Cohort | Phase 1b Escalation Dose/Schedule | |
|---|---|---|
| 3 | N 20 mg QD × 4 days per week (3 days off); weekly × 4 | VG 900 mg QD |

Primary Objectives
  Phase 1b: Determine the safety, tolerability, and R2PD of N+VG
  Phase 2: Evaluate the safety and tolerability of the R2PD and assess the objective response rate (ORR) by Recommendations for Initial Evaluation, Staging, and Response Assessment of Hodgkin and Non-Hodgkin Lymphoma: The Lugano Classification[7] (Lugano) and RECIL 2017[8] by central review
Secondary Objectives
  Phase 1b/2: Evaluate pharmacokinetics (PK) of N and PK of ganciclovir
  Phase 2: Evaluate time to tumor response, duration of response, time to tumor progression, and progression-free survival
Exploratory Outcomes
  Phase 1b/2: Evaluate changes in viral loads (CMV, EBV, HHV-6, HHV-8, HIV) as appropriate, EBV latency/lytic profile and genome methylation status, changes in his tone H3 acetylation (PBMCs)
Key Eligibility Criteria
  Relapsed/refractory, pathologically confirmed EBV+ lymphoma (EBER-ISH) or lymphoproliferative disease regardless of histologic subtype, including:
    EBV-associated post-transplant lymphoproliferative disease (PTLD) after allogeneic hematopoietic cell transplant (alloHCT) or solid organ transplant (SOT)
    EBV-associated lymphoproliferative disorders (LPD) and malignancies associated with acquired immunodeficiency, including HIV+ infections
    EBV-associated lymphomas and LPDs not associated with immunodeficiency
  Presence of measurable disease
  Age ≥18 years; ECOG performance status of 0 to 2; adequate hematologic, renal, and hepatic function The demographics of individuals enrolled in the trial are shown in Table 2 and the dosing by Cohort and intensity is shown in Table 3 below.

TABLE 2

Demographics and Lymphoma Characteristics

| Patients Enrolled (n) | 25 |
|---|---|
| Male/Female | 18/7 |
| Median Age, (Range), yrs | 58 (19-84) |
| ECOG PS, 0, 1, or 2 | 8, 15, 2 |
| Median Prior Therapies, n (Range) | 2 (1-9) |
| Irradiation | 6 |
| Transplant, n (%) [Auto, Allo, Both] | 9 [7, 1, 1] |
| HDACi | 3 (2 = Romidepsin, 1 Belinosat) |
| Median Day-1 Platelets, 10$^9$/L, (Range) | 174 (64-327) |

Lymphoma type

| B cell (12 total) | T-cell (8 total) |
|---|---|
| DLBCL (5) | Extranodal NK/T Cell Lymphoma (3) |
| Plasmablastic lymphoma (2) | Cutaneous T-cell lymphoma (1) |
| Burkitt's (1) | Anaplastic T cell (3) |
| Lymphoplasmacytic LPD (1) | Peripheral T-cell lymphoma not otherwise specified (1) |
| Post-transplant lymphoproliferative disorders (1) | |
| Other (2) | |
| Hodgkin's (5) | |
| HIV+ | 4 (20%) |

TABLE 3

Dosing by Cohort and Intensity

| Cohort | 1 | 2a | 2b | 2c |
|---|---|---|---|---|
| Total Daily Dose | N 20 mg VG 1800 mg | | N 10 mg VG 900 mg | |
| Schedule | 10 BID 900 BID | 5 BID 450 BID | 10 QD 450 BID | 10 QD 900 QD |
| Patients (n) | 7 | 5 | 4 | 4 |
| N 28-Day Median Daily Dose | 13.8 mg (69%) | 8.8 mg (88%) | 10 mg (100%) | 7.8 mg (78%) |
| Intensity, (%) [range] | [9.3-20] | [0-10] | [1-10] | [0-10] |

*VG starting dose adjusted for renal function per prescribing guidelines

Cohort 1 (10 mg, BID) exceeded the maximum tolerated doses based on 4 different hematologic dose limiting toxicities in 2 patients. No dose limiting toxicities and fewer dose holds were observed in cohort 2 (5 mg BID or 10 mg QD). Thrombocytopenia was the most common dose limiting toxicity as shown in Table 4. Platelet nadirs rapidly recovered after 3 to 5 days of dose hold. See FIG. 1. This indicated that treatment according to a schedule where patients were treated with HDACi for 1, 2, 3, 4, or 5 days; and not treated for 6, 5, 4, 3, or 2 day might limit hematologic side effects like thrombocytopenia.

TABLE 4

| Adverse Event | Cohort 1 (N = 7) [Nstat 20 mg, VGCV 1800 mg] | Cohort 2abc (N = 13) [Nstat 10 mg, VGCV 900 mg] | Cohort 3 (N = 5) + Phase 2 (N = 8) at the RP2D [Nstat 20 mg (4/7 d), VGCV 900 mg] N (%) |
|---|---|---|---|
| Hematologic | | | |
| Thrombocytopenia | 3 (43%) | 2 (15%) | 0 |
| Neutropenia | 2 (28%) | 2 (15%) | 1 (8%) |
| Anemia | 1 (14%) | 1 (8%) | 1 (8%) |
| Non-Hematologic | | | |
| Creatinine Elevation | 0 | 0 | 0 |
| Fatigue | 1 (14%) | 0 | 0 |

Nstat = nanatinostat; VGCV = valganciclovir; 4/7 d = 4 days of treatment in 7 day schedule Overall, Objective responses were observed in all dose cohorts and across B- and T-cell lymphomas. See Table 5. Evidence of antitumor activity was observed by PET in 10 of 18 patients evaluable by PET. Major responses have been observed at the first scan at week 8. Interestingly, pseudo-progression was observed in two patients at approximately month 4 were followed by major responses (CR, PR), and may indicate immune surveillance response. In two patients, progression in the skin was observed while maintaining a CR or PR systemic response. One patient who had skin clearing 2 weeks after therapy discontinued treatment and has remained disease free. In HIV+ patients, 3 of 3 evaluable have progressed

TABLE 5

| Best Response | All (n = 18) | HIV-negative | | | | |
|---|---|---|---|---|---|---|
| | | All | B Cell | T cell | NK cell | Hodgkin |
| CR | 5 | 5 | 2 | 1 | 1 | 1 |
| PR | 5 | 5 | 2 | 2 | 2 | 0 |
| SD | 4 | 4 | 1 | 0 | 0 | 3 |
| PD | 4 | 1 | 1 | 0 | 0 | 0 |
| Total | 18 | 15 | 5 | 3 | 3 | 4 |

CR = complete response;
PR = partial response;
SD = stable disease;
PD = progressive disease

Example 2—Nstat is More Potent than Other HDACi and Treatment Results in Long Term Histone Acetylation Nanatinostat has $T_{1/2}$ of approximately 2 hours, as shown in Table 6, in experiments conducted in humans. Patients enrolled in study were administered oral nanatinostat and valganciclovir at predefined doses. Blood samples for pharmacokinetic studies were drawn on cycle 1 day 1 at 30 minutes, 1, 2, 4, 6 and 24 hours after the first dose of nanatinostat. Serum concentration of nanatinostat were assayed at Inotiv, Inc. and PK parameters, including terminal half-life calculated using Phoenix WinNonlin v. 8.1 software.

The $IC_{50}$ of HDAC inhibition for nanatinostat, romidepsin (FK228), entinostat (MS-275), suberanilohydroxamic acid (SAHA or vorinostat), or trichostatin A (TSA) was determined in an in vitro histone acetylation assay. Briefly, all of the compounds are dissolved in DMSO. A series of dilutions of the compounds were prepared with 10% DMSO in HDAC assay buffer and 5 µl of the dilution was added to a 50 µl reaction so that the final concentration of DMSO is 1% in all of reactions. The compounds were pre-incubated in duplicate at RT for 1 hour in a mixture containing HDAC assay buffer, 5 µg BSA, HDAC enzyme (see Table 7) and a the particular HDACi. After 1 hour, the enzymatic reactions were initiated by the addition of HDAC substrate (BPS Bioscience) to a final concentration of 10 µM or 2 µM. The enzymatic reaction proceeded for 30 minutes at 37° C. After enzymatic reactions, 50 µl of 2×HDAC Developer was added to each well for the HDAC enzymes and the plate was incubated at room temperature for an additional 15 minutes. Fluorescence intensity was measured at an excitation of 360 nm and an emission of 460 nm using a Tecan Infinite M1000 microplate reader.

HDAC activity assays were performed in duplicates at each concentration. The fluorescent intensity data were analyzed using the computer software, Graphpad Prism. In the absence of the compound, the fluorescent intensity ($F_t$) in each data set was defined as 100% activity. In the absence of HDAC, the fluorescent intensity ($F_b$) in each data set was defined as 0% activity. The percent activity in the presence of each compound was calculated according to the following equation: % activity=$(F-F_b)/(F_t-F_b)$, where F=the fluorescent intensity in the presence of the compound.

The values of % activity versus a series of compound concentrations were then plotted using non-linear regression analysis of Sigmoidal dose-response curve generated with the equation $Y=B+(T-B)/1+10^{((Log\ EC50-X)\times Hill\ Slope)}$, where Y=percent activity, B=minimum percent activity, T=maximum percent activity, X=logarithm of compound and Hill Slope=slope factor or Hill coefficient. The $IC_{50}$ value was determined by the concentration causing a half-maximal percent activity.

TABLE 6

Geometric Mean (% CV) Single Dose Pharmacokinetics of VRx-3996 after Different Treatments

| Parameter | Treatment | | | | | | | |
|---|---|---|---|---|---|---|---|---|
| | A | | | B | | | C | |
| | N | Mean | % CV | N | Mean | % CV | N | Mean | % CV |
| $T_{max}$ (h)* | 4 | 3.00 (1.00-6.00) | | 9 | 2.00 (1.00-6.00) | | 6 | 1.00 (0.500-6.00) | |
| $C_{max}$ (ng/mL) | 4 | 18.5 | 230 | 9 | 62.6 | 138 | 6 | 78.9 | 46.3 |
| AUClast (ng-h/mL) | 4 | 40.5 | 204 | 9 | 165 | 128 | 6 | 227 | 37.8 |
| AUC (ng-h/mL) | 1 | 117 | NC | 1 | 317 | NC | 4 | 322 | 12.9 |
| Half-Life (h) | 1 | 2.18 | NC | 1 | 1.17 | NC | 4 | 1.67 | 21.1 |

A = 5 mg VRx-3996 p.o. and 450 mg Valganciclovir p.o.
B = 10 mg VRx-3996 p.o. and 450 mg Valganciclovir p.o.
C = 10 mg VRx-3996 p.o. and 900 mg Valganciclovir p.o.
*Median (range)

TABLE 7

| Assay | Enzyme Used (ng)/Reaction | Substrate |
|---|---|---|
| HDAC1 | 7.2 | 10 μM HDAC Substrate 3 |
| HDAC2 | 7.5 | 10 μM HDAC Substrate 3 |
| HDAC3/NCOR2 | 3.4 | 10 μM HDAC Substrate 3 |
| HDAC4 | 0.3 | 2 μM HDAC Substrate Class 2a |
| HDAC5 | 40 | 2 μM HDAC Substrate Class 2a |
| HDAC6 | 10 | 10 μM HDAC Substrate 3 |
| HDAC7 | 1.6 | 2 μM HDAC Substrate Class 2a |
| HDAC8 | 25 | 2 μM HDAC Substrate Class 2a |
| HDAC9 | 4.3 | 2 μM HDAC Substrate Class 2a |
| HDAC11 | 60 | 2 μM HDAC Substrate Class 2a |

Results for these experiments are shown in Table 8. Overall, in comparison to other HDACi, Nstat shows high potency inhibition of HDAC1, HDAC2, HDAC4, HDAC5, HDAC8, and HDAC9 when compared to all other HDACi tested.

TABLE 8

| | $IC_{50}$ (μM) or Percentage Inhibition | | | | |
|---|---|---|---|---|---|
| Enzymes | Nstat | FK228 | MS-275 | SAHA | TSA |
| HDAC1 | 0.0036 | 1.2 | 0.19 | 0.087 | — |
| HDAC2 | 0.012 | 8.4 | 0.31 | 0.099 | — |
| HDAC3/NCOR2 | 0.012 | 4.3 | 0.28 | 0.078 | — |
| HDAC4 | 1 | >100 NI* @ 100 μM | >100 NI @ 100 μM | >100 34% @ 100 μM | 4.5 |
| HDAC5 | 0.39 | >100 17% @ 100 μM | >100 NI @ 100 μM | ~48 | 3.4 |
| HDAC6 | 0.45 | 0.74 | ~66 | 0.011 | — |
| HDAC7 | 1.6 | >100 NI @ 100 μM | >100 NI @ 100 μM | >100 27% @ 100 μM | 1.4 |
| HDAC8 | 0.86 | ~63 | >100 NI @ 100 μM | ~46 | 1.6 |
| HDAC9 | 0.44 | >100 NI @ 100 μM | >100 NI @ 100 μM | >100 37% @ 100 μM | 4.1 |
| HDAC11 | 2.8 | >100 NI @ 100 μM | >100 NI @ 100 μM | ~49 | 2.1 |

Figure 2:
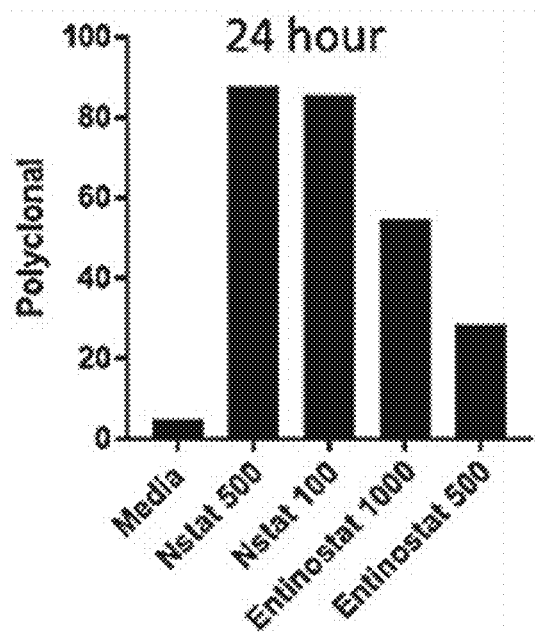
FIG. 2 shows comparison of the potency of nanatinostat and entinostat in peripheral blood mononuclear cells of healthy donors. Percentage of cells with H3 acetylation, as determined by flow cytometry, is shown.
Figure 3:
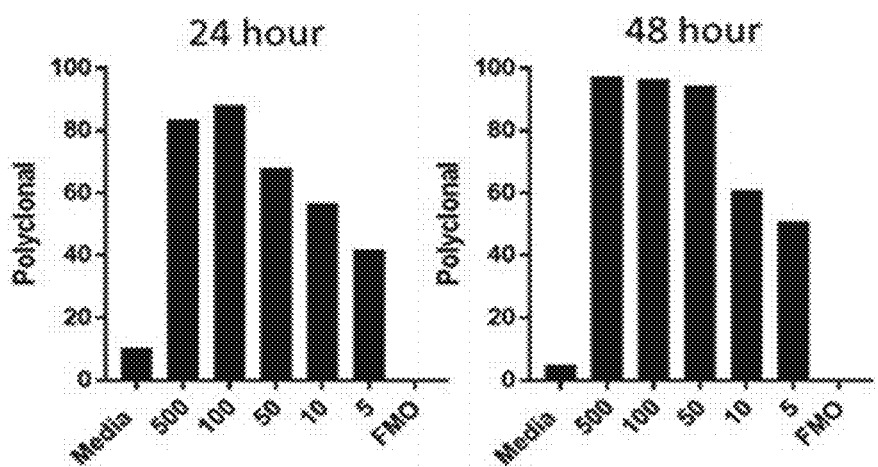
FIG. 3 shows time-course of H3 acetylation as a result of nanatinostat treatment in PBMC from healthy donors.

Nanatinostat has high potency as an HDAC and a short half-life compared to many HDACi. Given these properties nanatinostat might be able to be deployed on an intermittent schedule or a schedule with a dose hold. To determine if it was feasible to implement a dose hold from a pharmacokinetic standpoint the peripheral blood mononuclear cells were isolated from healthy volunteers and treated with either nanatinostat or entinostat (an HDACi with an elimination of half-life of approximately 36 hours). Since H3 acetylation is a pharmacodynamic biomarker of Nstat activity, acetylation of H3 was examined in treated cells. As shown in FIG. 2, Nstat was much more potent than entinostat in inducing elevated levels of Histone 3 acetylation, even at a dose of 100 nM. As shown in FIG. 3, this effect on H3 acetylation was long-lasting even at doses down to 10 nM.

Figure 4:
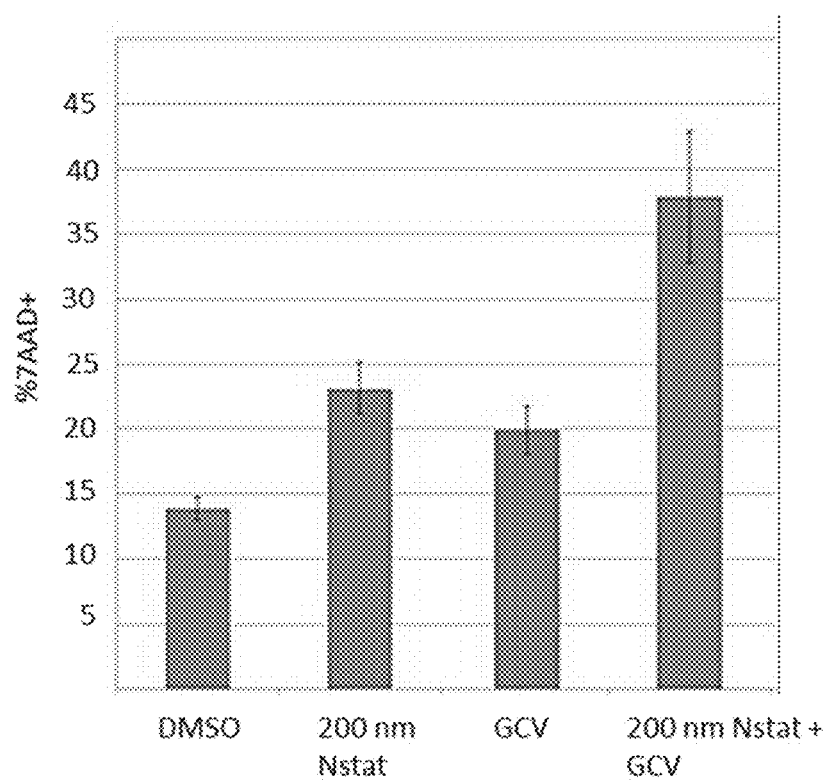
FIG. 4 shows the cytotoxic activity of nanatinostat was increased by ~40% when Nstat was combined with Ganciclovir. Additionally, this figure illustrates the duration of Nstat activity after 3 days of washout.

Nanatinostat increases cell cytotoxicity in an EBV infected cell line when combined with ganciclovir. This effect is seen even after Nstat removal as shown in FIG. 4. P3HR1 Burkitt's lymphoma cells were incubated with DMSO (solvent control) or Nstat for 3 days. After that time cell cultures were washed re-fed with ganciclovir (GCV) for an additional 3 days. All test conditions were run in triplicate. Cell death was measured by 7AAD staining.

Overall, these data and experiments provide rational that a dose holiday of an, HDACi like Nstat, can be implemented to adequately control adverse reactions while maintaining therapeutic efficiency.

Example 3—Clinical Trial Combining HDACi and Antiviral Treatment

The below example is a description of an open-label, dose escalation and expansion study of orally administered nanatinostat and valganciclovir in subjects with advanced, Epstein-Barr virus-associated solid malignancies.

Study Population
  Patients with locally advanced or metastatic, EBV-associated, solid tumors including, but not limited to:
    EBV-associated gastric adenocarcinoma
    EBV-associated nasopharyngeal carcinoma
Primary Objectives
  Determine the safety and tolerability of nanatinostat/valganciclovir
  Determine a recommended Phase 2 dose (RP2D) of nanatinostat/valganciclovir
  Assess activity based on objective response rate (ORR)
Secondary Objectives
  Evaluate pharmacokinetic (PK) parameters for nanatinostat
  Evaluate PK parameters for valganciclovir
  Evaluate time to response
  Evaluate duration of response
  Evaluate progression-free survival (PFS)
  Evaluate overall survival (OS)
Exploratory Objectives
  Evaluate changes in viral loads by quantitative polymerase chain reaction with treatment (cytomegalovirus, EBV) where applicable
  Evaluate EBV latency/lytic profile
Treatment Regimen
  The initial dose of nanatinostat will be 20 mg daily for 4 out of 7 days each week in a 4-week cycle, with dose escalation cohorts to 30 mg and 40 mg daily based on tolerability and lack of DLT. Valganciclovir will be administered continuously at 900 mg daily. The doses may be packaged in a weekly blister package. See FIG. 5.
Study Design
  A 2-part, Phase 1b/2 study to define a RP2D of nanatinostat in combination with valganciclovir (Phase 1b) and then to evaluate the efficacy of this combination in advanced solid malignancies (Phase 2). Phase 1b (dose escalation) will follow a rolling six design, in which up to 6 patients will be enrolled at each dose cohort:
    If 3 patients complete a 28-day cycle with no DLT, then the next cohort can be enrolled
    If 1 DLT is observed, the cohort will be expanded to include 6 to 8 patients.
    If 1 DLT in 6 patients is observed, then the cohort will be considered to have acceptable safety and the next cohort will be opened for enrollment.
    If 2 DLT in six patients are observed then the MTD has been exceeded.
  Patients who do not complete the first 28-day cycle for reasons other than study drug toxicity may be replaced. Phase 2 (expansion) up to 30 additional patients will be enrolled to confirm tolerability of the RP2D and ORR. All patients (Phase 1b and 2) will be assessed for response using RECIST 1.1 criteria. The clinical trial will enroll up to 50 patients.

Key Inclusion Criteria

Patients with a histologically or cytologically confirmed diagnosis of locally advanced or metastatic EBV-associated solid tumor for whom standard therapy is not effective, available, acceptable, or is intolerable Must have evaluable disease or at least one measurable lesion on computed tomography (CT) scan or magnetic resonance imaging (MRI) per RECIST 1.1

Males or females aged ≥18 years at screening

Screening laboratory values:
  Hemoglobin ≥9 g/dL
  Absolute neutrophil count ≥1500 cells/mm3
  Platelet count ≥100,000 cells/mm3
  Total bilirubin ≤1.5×ULN
  Aspartate aminotransferase and alanine aminotransferase ≤2.5×ULN. (unless liver metastases are present then up to 5×ULN allowed)
  Serum creatinine ≤1.5 mg/dL or estimated glomerular filtration rate (eGFR) ≥60 mL/min/1.73 m2
  International Normalized Ratio (INR) or Prothrombin Time (PT) ≤1.5×ULN (unless patient is receiving anticoagulant therapy as long as PT or PTT is within therapeutic range of intended use of anticoagulants)
  Activated Partial Thromboplastin Time (aPTT) ≤1.5× ULN (unless patient is receiving anticoagulant therapy as long as PT or PTT is within therapeutic range of intended use of anticoagulants)

Patients with treated, stable CNS metastases (including leptomeningeal carcinomatosis) are allowed, if there is no evidence of progression for at least 4 weeks after CNS-directed treatment as ascertained by clinical examination and brain imaging. The use of seizure prophylaxis is allowed Resolution of any clinically significant toxic effects of prior therapy to Grade 0 or 1 according to the National Cancer Institute Common Terminology Criteria for Adverse Events (NCI CTCAE), version 5.0 (exception of alopecia and Grade 2 peripheral neuropathy)

Eastern Cooperative Oncology Group (ECOG) performance status of ≤2

Example 4—Nanatinostat Tablet Formulation

According to the methods and kits described herein, Nanatinostat can be formulated as a single agent, immediate release tablet. Non-limiting examples of formulations of dosages in a single agent tablet are shown in Table 10 below. The manufacturing process is a typical pharmaceutical granulation/blend/compression/coating process.

TABLE 9

| | | | Formula | | |
|---|---|---|---|---|---|
| Materials | Function | % w/w | Weight per Tablet (5 mg) | Weight per Tablet (10 mg) | Weight per Tablet (20 mg) |
| Nanatinostat | Active Pharmaceutical Ingredient | 5.00 | 5.00 | 10.00 | 20.0 |
| Mannitol | Filler | 25.00 | 25.00 | 50.00 | 50.0 |
| Microcrystalline Cellulose | Filler | 65.50 | 65.50 | 131 | 262.0 |
| Croscarmellose Sodium | Disintegrant | 4.0 | 4.0 | 8.0 | 16.0 |
| Sodium Stearyl Fumarate | Lubricant | 0.5 | 0.5 | 1 | 2 |
| Total of tablet core: | | 100.00 | 100 mg | 200 mg | 400 mg |
| Non-functional coating | | | 3 mg | 6 mg | 12 mg |
| Total of coated tablet | | | 103 mg | 206 mg | 412 mg |

Example 5—Co-Formulations of HDACi and Antivirals

Experiments were undertaken to develop immediate release, fixed dosing tablet formulations with an anti-viral and an HDACi. These experiments evaluated Bulk/Tap Density, Particle Size Distribution, Blend Uniformity, Hardness, and Disintegration time of Tablets. A granulation/blend/compression/coating pharmaceutical manufacturing process was developed to manufacture fixed dose tablets with various ratio and strength. One embodiment of fixed dose tablet of 20 mg Nanatinostat/450 mg Valganciclovir is shown in Table 10.

TABLE 10

Fixed dose tablet of 20 mg Nanatinostat/450 mg Valganciclovir

| Ingredients | % w/w | mg/tablet |
|---|---|---|
| Valganciclovir Hydrochloride | 79.4% | 496.30 (450 free base equivalent) |
| Nanatinostat | 3.2% | 20.00 |
| Microcrystalline Cellulose | 10.2% | 63.20 |
| Povidone | 2.2% | 14.00 |
| Crospovidone | 3.4% | 21.00 |
| Magnesium Stearate | 1.6% | 10.50 |
| Total | 100% | 625.0 |

The dissolution profile of fixed dose tablet of 20 mg Nanatinostat/450 mg Valganciclovir is shown in Table 11.

TABLE 11

Dissolution of Fixed dose tablet of 20 mg Nanatinostat/450 mg Valganciclovir

| Nanatinstat Dissolution | | Valganciclovir Dissolution | |
|---|---|---|---|
| Time point (min) | % Release | Time point (min) | % Release |
| 10 | 12 | 10 | 46 |
| 20 | 30 | 20 | 75 |

TABLE 11-continued

Dissolution of Fixed dose tablet of 20 mg Nanatinostat/450 mg Valganciclovir

| Nanatinstat Dissolution | | Valganciclovir Dissolution | |
|---|---|---|---|
| Time point (min) | % Release | Time point (min) | % Release |
| 30 | 47 | 30 | 90 |
| 45 | 64 | 45 | 100 |
| 60 | 75 | 60 | 102 |
| 75 | 82 | 75 | 102 |
| 90 | 89 | — | — |

Experiments were also conducted to manufacture the tablet with different strengths and ratios, evaluate any process modifications and optimize the powder blend for flow properties, particle size and density. The resultant tablets from the final blend were characterized physically (Compression Profile) chemically (Assay/Impurities, Water Content, Dissolution) and placed on long term stability studies. The formulation formula of two, immediate release, fixed dose tablets, i.e, 10 mg Nanatinostat/450 mg Valganciclovir and 20 mg Nanatinostat/900 mg Valganciclovir are shown in Table 12.

TABLE 12

| Fixed dose tablets Material | % w/w | 10 mg Nanatinostat/450 mg Valganciclovir mg/tablet | 20 mg Nanatinostat/900 mg Valganciclovir mg/tablet |
|---|---|---|---|
| Nanatinostat | 1.6 | 10.0 | 20.0 |
| Valganciclovir HCL | 79.4 | 496.3 (450 free base equivalent) | 992.6 |
| Microcrystalline Cellulose | 11.8 | 73.2 | 146.4 |
| Povidone K30 | 2.2 | 14.0 | 28.0 |
| Crospovidone | 3.4 | 21.0 | 42.0 |
| Magnesium Stearate | 1.6 | 10.50 | 21.0 |
| Total | 100.0 | 625.0 | 1250 |
| Coating | | | |
| Non-functional coating | 3.0 | 18.8 | |
| Total | 103.0 | 643.8 | |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:

1. A method of treating an Epstein-Barr virus associated lymphoproliferative disorder in an individual, the method comprising administering to the individual: (a) nanatinostat at a total daily dose from 10 milligrams to 20 milligrams per day; and (b) an effective amount of an antiviral agent selected from the list consisting of aciclovir, ganciclovir, valaciclovir, valganciclovir, and famciclovir, wherein the individual is treated according to a treatment schedule having a duration of one week, and wherein the individual is administered nanatinostat for 4 days of the treatment schedule, thereby treating the Epstein-Barr virus associated lymphoproliferative disorder.

2. The method of claim 1, wherein the nanatinostat is administered at a total daily dose of 10 milligrams.

3. The method of claim 1, wherein the nanatinostat is administered at a total daily dose of 20 milligrams.

4. The method of claim 1, wherein the nanatinostat is administered once per day.

5. The method of claim 1, wherein the nanatinostat is administered twice per day.

6. The method of claim 1, wherein the antiviral agent is valganciclovir.

7. The method of claim 6, wherein the valganciclovir is administered at a total daily dose of 1,800 milligrams.

8. The method of claim 6, wherein the valganciclovir is administered at a total daily dose of 900 milligrams.

9. The method of claim 6, wherein the valganciclovir is administered at a total daily dose of 450 milligrams.

10. The method of claim 1, wherein the antiviral agent is administered every day of the treatment schedule.

11. The method of claim 1, wherein the antiviral agent is not administered on one or more days of the treatment schedule.

12. The method of claim 1, wherein the antiviral agent is administered once a day.

13. The method of claim 1, wherein the antiviral agent is administered twice a day.

14. The method of claim 1, wherein the antiviral agent is administered orally.

15. The method of claim 1, wherein the nanatinostat is administered orally.

16. The method of claim 1, wherein the treatment schedule is repeated.

17. The method of claim 1, wherein the Epstein-Barr virus associated lymphoproliferative disorder is an Epstein-Barr virus associated leukemia or a lymphoma.

18. The method of claim 17, wherein the leukemia or lymphoma is a B cell or a T cell leukemia or lymphoma.

19. The method of claim 1, wherein the individual is afflicted with thrombocytopenia.

20. The method of claim 1, wherein the individual has a platelet count of less than 150,000 platelets per microliter.

21. A method of treating an Epstein-Barr virus associated lymphoproliferative disorder in an individual, the method comprising administering to the individual (a) nanatinostat at a total daily dose of about 20 mg; and (b) valganciclovir at a total daily dose of about 900 mg according to a weekly treatment schedule, wherein the individual is administered nanatinostat for 4 consecutive days of the treatment schedule, and valganciclovir is administered every day of the treatment schedule.

22. The method of claim 21, wherein nanatinostat and valganciclovir are administered orally.

23. The method of claim 21, wherein nanatinostat and valganciclovir are each administered once a day.

24. The method of claim 21, wherein nanatinostat and valganciclovir are each administered twice a day.

25. The method of claim 21, wherein the treatment schedule is repeated.

* * * * *